United States Patent [19]

Descales et al.

[11] Patent Number: 5,712,797
[45] Date of Patent: Jan. 27, 1998

[54] PROPERTY DETERMINATION

[75] Inventors: Bernard Descales, Marseille; Didier Lambert, Saint-Mitre-Les-Remparts; Jean-Richard Llinas, Marseille; Andre Martens, Chateauneuf-Les-Martigues; Sebastien Osta, Istres; Michel Sanchez, Lavera, all of France

[73] Assignees: BP Chemicals Limited; BP Oil International Limited, both of London, England

[21] Appl. No.: 465,680

[22] Filed: Jun. 6, 1995

[30] Foreign Application Priority Data

Oct. 7, 1994 [GB] United Kingdom ............... 94430009

[51] Int. Cl.$^6$ ............................ G01N 21/35; G01J 3/42
[52] U.S. Cl. ............................ 364/499; 364/496
[58] Field of Search ............................ 364/496, 497, 364/498, 499, 500, 501, 502, 554; 73/23.2, 25.01, 29.01, 30.01

[56] References Cited

U.S. PATENT DOCUMENTS

| | | |
|---|---|---|
| 3,896,312 | 7/1975 | Brown et al. |
| 3,997,786 | 12/1976 | Lauer et al. |
| 4,251,870 | 2/1981 | Jaffe |
| 4,766,551 | 8/1988 | Begley |
| 4,882,755 | 11/1989 | Yamada et al. |
| 5,023,804 | 6/1991 | Hoult |
| 5,082,985 | 1/1992 | Crouzet et al. |
| 5,121,337 | 6/1992 | Brown |
| 5,153,140 | 10/1992 | Langfeld et al. |
| 5,225,679 | 7/1993 | Clarke et al. |
| 5,262,961 | 11/1993 | Farone |
| 5,311,445 | 5/1994 | White ............... 364/498 |
| 5,361,912 | 11/1994 | Krieg et al. |
| 5,446,681 | 8/1995 | Gethner et al. ............... 364/554 |
| 5,452,232 | 9/1995 | Espinosa et al. |
| 5,475,612 | 12/1995 | Espinosa et al. |

FOREIGN PATENT DOCUMENTS

| | | |
|---|---|---|
| 304232 | 2/1989 | European Pat. Off. |
| 305090 | 3/1989 | European Pat. Off. |
| 345182 | 12/1989 | European Pat. Off. |
| 437 829 A1 | 7/1991 | European Pat. Off. |
| 607048 A1 | 7/1994 | European Pat. Off. |
| 625702 A1 | 11/1994 | European Pat. Off. |
| 631810 A1 | 1/1995 | European Pat. Off. |
| 2626579 | 8/1989 | France |
| WO92/07326 | 4/1992 | WIPO |
| WO93/20429 | 10/1993 | WIPO |
| WO94/08226 | 4/1994 | WIPO |

OTHER PUBLICATIONS

"Multicomponent Analysis of FT-IR Spectra" (*Applied Spectroscopy*; vol. 45; No. 6; P. Saarinen and J. Kauppinen; pp. 953-963; ©1991).

"Computer Searching of Infrared Spectra Using Peak Location and Intensity Data" (*Analytical Chem.*; vol. 48; No. 4; R. C. Fox; pp. 717-721; ©1976).

(List continued on next page.)

*Primary Examiner*—Emanuel T. Voeltz
*Assistant Examiner*—M. Kemper
*Attorney, Agent, or Firm*—Fay, Sharpe, Beall, Fagan, Minnich & McKee

[57] ABSTRACT

A method of determining or predicting a value $P_x$ of a property (e.g. octane number) of a material X or a property of a product of a process from said material or yield of said process, which method comprises measuring the absorption $D_{ix}$ of said material at more than one wavelength in the region 600-2600 nm, comparing the said absorptions or a derivative thereof with absorptions $D_{im}$ or the derivatives thereof at the same wavelength for a number of standards S in a bank for which the said property or yield P is known, and choosing from the bank at least one standard $S_m$ with property $P_m$ said standard having the smallest average value of the absolute difference at each wavelength i between the absorption $D_ix$ (or derivative thereof) for the material and the absorption $D_im$ (or derivative thereof) for the standard $S_m$ to obtain the $P_x$, with averaging of said properties or yields $P_m$ when more than one standard $S_m$ is chosen.

32 Claims, 1 Drawing Sheet

OTHER PUBLICATIONS

"On-Line NIR Analysis and Advanced Control Improve Gasoline Blending" (*Oil Gas J.*; vol. 92; No. 42; A. Espinosa et al.; pp. 49–56; ©1994).

"Online Process Analyzers" (*Chemical Engineering*; vol. 83; No. 13; V.C. Utterback; pp. 141–144; ©1976).

"The Design of Calibration in Near Infra-Red Reflectance Analysis by Clustering"; *Journal of Chemometrics*; vol. 1; T. Naes; pp. 121–126; ©1987.

"Selection of Samples for Calibration in Near-Infrared Spectroscopy. Part II: Selection Based on Spectral Measurements"; *Applied Spectroscopy*; vol. 44, No. 7; T. Isaksson and T. Naes; pp. 1152–1158; ©1990.

"Nonlinear Multicomponent Analysis by Infrared Spectrophotometry"; *Analytical Chemistry*; vol. 55; M. Maris and C. Brown; pp. 1624–1702; ©1983.

"Near-Infrared Spectrum Qualification via Mahalanobis Distance Determination"; *Applied Spectroscopy*; vol. 41, No. 7; R. G. Whitfield et al.; pp. 1204–1213; ©1987.

"Selection of Calibration Samples for Near-Infrared Spectrometry by Factor Analysis of Spectra"; *Analytical Chemistry*; vol. 60, No. 6; G. Puchwein; pp. 569–573; ©1988.

"Unique Sample Selection via near-Infrared Spectral Subtraction"; *Analytical Chemistry*; vol. 57; No. 12; D. E. Honigs et al.; pp. 2299–2303; ©1985.

PROPERTY DETERMINATION

This invention relates to a method of determining or predicting by near infra red (NIR) spectroscopy properties of feeds or products and/or yields in physical or chemical processes or separations, in particular involving hydrocarbons, especially in hydrocarbon refineries

BACKGROUND OF THE INVENTION

NIR spectroscopy has many advantages over other methods of analysis in refineries and can cover a large number of repetitive applications accurately, quickly and on line. The NIR region between 800 and 2500 nm contains the totality of molecular information in the form of combinations and overtones from polyatomic vibrations, but Mathematical techniques are needed to exploit this information and to calculate the desired parameters. U.S. Pat. Nos. 5,490,085; 5,452,232; and 5,475,612 the disclosure of which is hereby incorporated by reference, describe the use of NIR for determining octane number, yields and/or properties of a product of a chemical process or separation process from analysis on the feeds to that process, and yields and/or properties of a product of a blending operation again from analysis on the feed thereto.

At present, numerical methods described for modelling physicochemical properties based on NIR spectra all are of a correlative nature and involve relations of a regressional character between the property(ies) studied. Among these multivariable analyses are multilinear regression (MLR), Principle Component Regression (PLR), Canonic regression, and regression by Partial Least Squares (PLS). In all cases there is sought between the property and the NIR spectrum a relation which may be linear but is usually quadratic or of higher algebraic form involving regression coefficients applied to each absorption. The establishment of any regression requires a progressive calibration, as the approach is empirical and not supported by a theory.

These techniques have disadvantages, the chief of which is the need for establishing a strong correlation between the spectrum and the property, and their difficulty in dealing with positive or negative synergy between components contributing to that property. For example for determining chemical composition e.g. LINA (linear, isoparaffin, Naphthenic, Aromatics) in a hydrocarbon feed to a catalyst reformer, a PLS technique based on the NIR spectra has been described for use. The model works well on the calibration set but the response of the models when pure hydrocarbons are added e.g. cyclohexane is not satisfactory, as the model predicts changes in isoparaffins and naphthenes the reverse of that found experimentally Furthermore there are other practical difficulties, mainly in the need to identify samples of families having the same kind of relation between the spectra and the properties to be modelled. Thus the model may be limited especially with a non linear relation between spectrum and property. Especially when at the edges of the available data the accuracy of the model diminishes. The stability of the model is also a problem, as is the need when adding new standards to do laborious revisions to give the new model, especially when adjusting to a new feedstock for a process; thus testing 6 properties on 4 products leaving a distillation unit requires 24 models, each of which has to be changed for each change of the feed not included in the calibration.

We have discovered a new approach avoiding the above problems with correlations, and regression calculations, and being capable of being expanded automatically with use of a new product of different quality.

SUMMARY OF THE INVENTION

The present invention provides a method of determining or predicting a value Px, of a property of a material X or a property of a product of a process from said material or yield of said process, which method comprises measuring the absorption $D_i x$ of said material at more than one wavelength in the region 600–2600 nm, comparing the said absorptions or a derivative thereof with absorptions $D_i m$ or derivatives thereof at the same wavelengths for a number of standards S in a bank for which the said property or yield P is known, and choosing from the bank at least one and preferably at least 2 standard $S_m$ with property $P_m$, said standard $S_m$ having the smallest average values of the absolute values of the difference at each wavelength i between the absorption $D_i x$ (or derivative thereof) for the material and the absorption $D_i m$ (or derivative thereof) for the standard $S_m$ to obtain value $P_x$, and with averaging of said properties or yields Pm, when more than 1 standard $S_m$ is chosen.

The above method can be performed without regression or correlation techniques.

BRIEF DESCRIPTION OF THE DRAWINGS

The invention is illustrated in the accompanying Figures in which:

In FIG. 1, an optical fibre or tube 3 links a spectrometer 2 and a probe 6 in or at process line 1. The spectrophotometer 2 produces absorbance signals at more than 1 wavelength, which signals are passed via line 4 to computer 5, where the signals as such or after conversion to one or more derivative signals, are used to enable the computer to access the databank 7 of standard absorptions and properties/yields therein. The signals are compared to those of the standard absorptions as described above and one or more standard absorption(s) and its/their corresponding property(ies) or yield(s). The output of the computer 5 may be in the form of spectral absorbancies or a property or yield of the product in line 1 and may be printed in hard copy. Preferably however, the output as a signal is used to control the process involved with the product in line 1. i.e. for which line 1 is a feed or a product line; in this case the computer 9 is linked to and instructs the controller 9 which, via line 10, controls that process by acting on operating conditions e.g. via valves/temperature and/or pressure controls in line 1 or in relation to line 1. By this means the property or yield of product in line 1 can be optimized.

In FIG. 2, the initial operation 11 is to measure the absorption of the unknown, after which in the second step 12, the absorptions are compared to absorptions in spectra of standards, and in the third step 13, the spectra of the standards Sm are chosen according to criteria described above, and then in step 14, the property(ies) of the standard (s) Sm chosen is used to obtain the desired property or yield. If the spectrum of only 1 standard Sm is chosen, then the value $P_x$ of the unknown is the same as that of that standard Pm. If more than 1 spectrum is chosen, the value $P_x$ of the unknown is the average of the values Pm of the standards. If desired in an optional step 15, the value $P_x$ is compared to the desired value for the unknown and in step 16 the process involving the unknown is adjusted to make the value $P_x$ the same as the desired value.

DETAILED DESCRIPTION OF THE INVENTION

Figure 1:
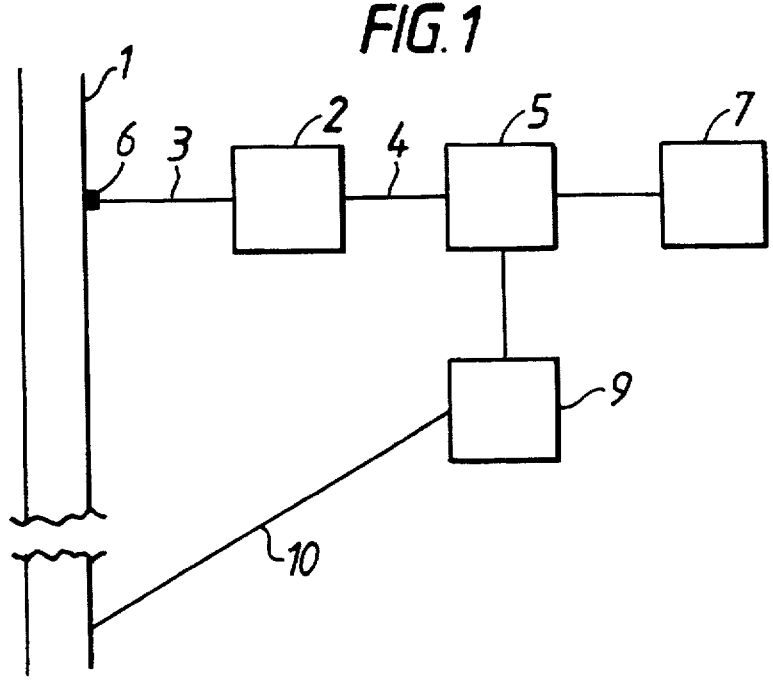
FIG. 1 represents a schematic diagram showing apparatus for use in the invention.
Figure 2:
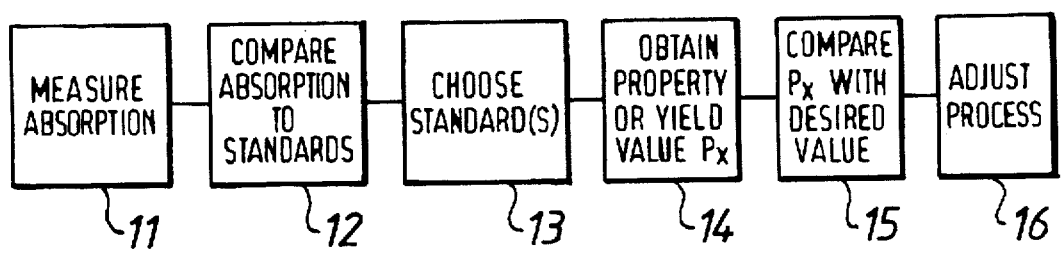
FIG. 2 represents a schematic block flow diagram for the method of the invention.

Thus for the performance of the method of the invention, a bank is prepared in which the NIR spectra are recorded at many wavelengths for a large number of standard materials, together with their properties (or those of products obtained by processes therefrom) determined by alternative techniques e.g. gaschromatography for chemical compositions and yields determined by known methods. The standards are chosen to cover the area in which the method is to be used, so for octane number determination, a range of gasolines is chosen of widely varying octane numbers, with different contents of lead, or other additives such as alkyl ethers and aromatics. The number of wavelengths chosen may be 2–1000 e.g. 5–200 or 10–20 such as 40–80 while the number of standards can be at least 100 or 1000, or 100,000 up to 5 million depending on property(ies) chosen.

The wavelengths chosen may be at regular intervals such as each 1–50 or 15–35 nm (or each 1–5 nm or each nanometer) or may be at irregular intervals e.g. with intervals of 1–200 nm e.g. 1–100 or 1–50 such as 4–50 or 10–60 nm, which may be random or chosen because of a change in the shape of the spectral curve at that wavelength e.g. a peak, trough or shoulder. The wavelengths may be in the region 600–2600 nm, such as 800–2600 nm, in particular 1500–2600 or 2000–2550 nm, or 800–2000 especially 1000–1800 nm for diene containing gasolines such as ones produced by cracking e.g. steam cracking. The wavenumbers may be in the region 16,600–3840 $cm^{-1}$, e.g. 12,500 to 3840 $cm^{-1}$ in particular 6660–3840 or 5000–3900 $cm^{-1}$, or 12500–5000 especially 10000–5500 $cm^{-1}$; corresponding frequencies in Hertz can be obtained by multiplying this wavelength by $3\times10^{10}$ cm/sec.

The absorptions for the unknown sample are compared with the absorptions at the same wavelength of the standards, and those standards chosen having the smallest differences. The properties of those chosen standards are then averaged to determine the property of the unknown sample. The absorptions at more than one wavelength may be chosen, e.g. 2–1000 such as 5–100 or 10–20.

In the method of the invention the standards chosen are those with the smallest average values of the absolute difference at each wavelength i between the absorption/optical density (or a derivative thereof) $D_{ix}$ for the unknown material and the corresponding absorption/optical density (or derivative thereof) $D_{im}$ for the standard. The averages may be in respect of the mean value of $D_{ix}-D_{im}$ (whatever its sign i.e. absolute diference), or $(D_{ix}-D_{im})^2$ and may be the simple mean value or the differences may be weighted to take account of the different sensitivity of the absorption to the property at that wavelength or the different sensitivity of the spectrometer at that wavelength. For each standard in the bank of standards for the type of material in question, the average difference is found as described and the standard or standards with the smallest average differences chosen, e.g. at least 1 but preferably at least 2 such as upto 1000 smallest such as 1 (or 2)–100 or 1 (or 2)–20 but is particular 1 (or 2)–10 and especially 2–6 smallest. Advantageously the average differences chosen and hence the standard (or standards) $S_m$ chosen for the property or yield wanted are such that in relation to the unknown material X and each chosen standard $S_m$ the following functions is met $$\frac{i_{xm}}{\Sigma D_{ix}} < \text{experimental error}$$

wherein $i_{xn}$ is the proximity index and is defined by $i^2(xm) = \Sigma(D_{ix}-D_{im})^2$ and the experimental error is in determining said property or yield in the standard. The value $P_x$ of the property or yield is the same as property or yield $P_m$ or the average $P_m$ if more than one standard $S_m$ is chosen.

In order to aid the choice of the appropriate standards, especially in relation to a large number of wavelengths for a complex unknown mixture, it is preferred to limit the choice to those defined by means of a minimal index. For the chosen standard the minimal index is at least the same as the differences between the absorptions of the unknown and the standards. Mathematically, this may be expressed as $i^2ab \leq i^2M$ where iM is the minimal index for the property, and iab is a measure of the deviation (called the proximity index) at all the chosen wavelengths between absorption of the unknown and a chosen standard b. That measure is defined by $$i(ab)^2 = \Sigma_i(D_{ia}-D_{ib})^2 \quad (1)$$

where $D_{ia}$ is the optical density (or absorbence) of unknown a at wavelength i (or a derivative thereof e.g. a first, second or third derivative of that density), and $D_{ib}$ is the optical density (or absorbence) of standard b at that wavelength i (or a derivative thereof e.g. a first, second or third derivative of that density). The value of $D_i$ is the optical density or the optical density difference with respect to the baseline of the spectrum at that wavelength, or the baseline interpolated between 2 wavelengths on either side thereof.

If desired instead of the optical density $D_i$ a normalized density $W_i$ may be used where $W_i=D_i/\Sigma D_i$. This normalization avoids errors due to small electronic fluctuations in the apparatus and compensates for small differences in the optical path between the optical cells. In this case the proximity index is defined by $$i(ab)^2 = \Sigma_i(W_{ia}-W_{ib})^2 \quad (2)$$

The indices can be weighted as desired for increasing resolution. One approach is to define the indices as follows.

$$i(ab)^m = \Sigma Abs \text{ value } (X_{ia}-X_{ib})^m/\sigma_i^n \quad (3)$$

where $X_i$ is $D_i$ or $W_i$ or a mathematical combination thereof, $\sigma_i$ is the standard deviation of X for the set of samples considered (at that wavelength) and each of m and n which are the same or different is weighting factor which is positive but can be a whole number or a fraction. Other variants can be used with other weighting factors such as those involving the spectral experimental error $e_i$, where $e_i$ is the reproducibility of the spectral measurement at wavelength i. The choice between the different options for the weighted indices may be dictated by numerical efficiency.

The reproducibility of the experimental measurements in the standards may be at least 90% or 94% or 95%. The minimal index may be obtained from a reference standard samples set according to the following procedure, hereafter called the Minimal Index Procedure. The NIR spectra for 2 standard samples A and B and their property P e.g. Octane Number are determined. By means of equation (1), (2) or (3), the value of the proximity index $i_{ab}$ is determined via the absorptions at a series of wavelengths; this index is applicable to the difference in properties $P_a-P_b$ called $EP_{ab}$. This process is repeated with other pairs of standards c and d, e and f etc to obtain a series of Proximity Indices $i_{cd}$ etc with corresponding property differences $EP_{cd}$ etc. For different values of a parameter L which is greater than the indices $i_{ab}$ etc, the corresponding values of $EP_{ab}$ etc are averaged to give an average $EP_{ij}$ for that value of L; the different values of $EP_{ij}+t\sigma/\sqrt{K}$ are then plotted on a graph against L $\sigma$ is the accuracy of the property determination and K is the number of pairs of samples for which $i_{ab}$ is inferior to a given L. t is the Student factor at a given level of confidence. The intercept is then measured between the curve obtained and a line usually horizontal which is the reproducibility of the property level at an appropriate confidence interval e.g. 90% or more usually 95%; the abcissa portion of the intercept gives the minimal index $i_{min}$, which is the minimum value of $i_{ab}$ for which $P_a=Pb$ within the frame of experimental error.

From this minimal index by Procedure 1, the standards can be chosen which have values of $i^2_{ab} \leq i^2_{min}$ where in this case a is the unknown and b is a standard, as in this case the difference between Property a and Property b is less than or equal to $\sigma\sqrt{2}$, where $\sigma$ is the experimental error in measuring the property. Then from the property P value or values of the chosen standard, the property of the unknown is obtained directly or by averaging those values, usually the arithmetic mean, but optionally with weighting.

The method of the invention may be used to determine more than one Property P at once, e.g. at least 2, such as 1-30 e.g. 2-10 properties at once. Each property of the standards has a particular unweighted, minimal index, which may lie in the region $0-10^{-10}$ e.g. $10^{-2}$ to $10^{-8}$, in particular $5\times10^{-7}$ to $5\times10^{-4}$. If the Minimal Index chosen is the smallest for all the properties desired, then the same one may be used for all the properties and the standards chosen will be suitable for all the properties. The Minimal Index for each property may be used separately, with different numbers of standards chosen for each property (assuming different Minimal Indices). If desired the same Minimal Index may be used, which is not the smallest, resulting in some of the chosen standards (with a higher Minimal Index) giving some properties of high accuracy and some (with a lower Minimal Index) giving some properties of less high accuracy.

The property to be determined may be of the sample being analyzed or a product obtained from that sample e.g. a product of blending or cracking the sample, as the property value obtained is derived from the standards, and they will have been determined as needed for the eventual use. Our U.S. Pat. Nos. 5,452,232 and 5,475,612 referred to above describes such techniques when applied to use of NIR with correlation to blending or cracking operation; the same principles apply in the present method.

If the density of the standards in the data bank is sufficient to have $i^2ab \leq i^2$ min as is usually the case, the above procedure is very satisfactory. But there are occasions when the bank is incomplete, because of shortage of data of properties in a particular area i.e. a low density of standards or the sensitivity of the property to changes in absorption is so small, that a very small Minimal Index is required and there may be few standards with proximity indices meeting it. It is possible simply choose a larger Minimal Index with e.g. 1-5 times such as 1.5-2 times the Minimal Index; the results may be less accurate than those from a smaller minimal index.

However, a more accurate approach with a low density of standards involves a special densification process of Procedure 2, in which random or semi random densification of the neighbourhood of the unknown is achieved by generation of synthetic standards, based on standards already in the bank. Each new synthetic standard may be obtained from combinations of standards taken at random from the bank but preferably it is obtained from the other standards by the constraint of choosing only a mixture of N standards for which $$(Min)C_j-u_j \leq C_j \leq (Max)C_j+u_j \qquad (4)$$

and $$\Sigma C_j=1 \qquad (5)$$

where $C_j$ is the fraction of component j in the sample i.

Min $C_j$ is the minimum amount of j in the initial industrial calibration mixture or in the samples for which the method is to be used.

Max $C_j$ is the maximum amount of j in the initial industrial calibration mixture or in the samples for which the method is to be used.

uj is usually between 1 and 0.01 preferably between 0.5 and 0.1 and can be fixed for each property.

The constraints over the choice of such mixtures of N standards can also be equally fixed in the spectral area from which the samples will be drawn in order to remain in the areas of similar chemical nature.

The number of samples effectively drawn into the bank in this densification can be of several thousand generally 1000-2000. The calculation time is extended without significant deterioration in the results. If no further neighbours are found, the trawl of new samples drawn in is enlarged.

The spectrum of each mixture is calculated by the combination of the spectra of the standards used according to the formula $$S_{Mi}=\Sigma C_{ij}XS_j \qquad (6)$$

where $S_j$ is the spectrum in the mixture of component j in the calibration matrix.

The properties of each mixture PMi can be calculated by a generally linear combination of the properties of the standards according to the formula $$P_{Mi}=\Sigma C_{ij}XP_j \qquad (7)$$

where $P_j$ is the property of component j

In the case of non linear additive properties, appropriate mixing factors can be applied e.g. by blending factors or similar for density and viscosity.

Having obtained the spectrum and the properties of the synthetic mixtures, these can be used as "standards" to help determine the properties of an unknown sample in the same way as a conventional standard.

Instead of using either of the two above approaches, 1-7, a third type Procedure 3 may be used as follows. The Q nearest samples to unknown X can be found from a selection from the bank samples for which the proximity index to the unknown sample is (V) X $i_{min}$) where v is $0.1<v<10$, (8) preferably $0.5<v<2$ or $1 \leq v \leq 5$. Then by the method of least squares is found a generally linear combination of the standard products, which are the Q nearest samples to reproduce the spectrum of X according to the equation.

$$S_x=\Sigma C_R XS_r \qquad (9)$$

where $C_r$ is the coefficient for sample R in the total Q and $S_R$ is the spectrum of sample R. The coefficient $C_R$ which can be normalized to $C_R=1$ or not and/or optimized by the least squares route, allows an estimation of the property $P_x$ according to the equation.

$$P_x=\Sigma C_R XP_R \qquad (10)$$

where $P_R$ is the property of sample R.

The eventual size of the estimation error can be derived by application of Gaussian theory, also called the propagation error (see Eq. 10).

The above third approach can only be applied if the product X is situated inside the maximum extension of the standard products defined by equation (8). If this is not the case, X is outside the field of the actual bank of products and escapes from the area of knowledge of the method into the area of learning.

The densification process described in relation to equations 4–7, or 9 or 10 is usually applied to the method of the invention involving no correlation or regression techniques. However, if desired the densification process may be applied to increase the number of "standards" for consideration in an NIR analytical technique involving the correlation on regression techniques as described above e.g. MLR. The present invention also provides a method for adding an extra synthetic standard to a bank of known standards, each of which relates at least one absorption in the 600–2600 nm region (or derivative thereof) of a known material to a known property related to that material, which method comprises choosing from the bank at least 2 standards for which equations 4 and 5 above are met, considering mixing the chosen standards in at least one proportion to produce at least one mixture for use as a synthetic standard, and estimating the spectrum and property of said mixture according to equation 6 and 7 respectively.

The spectrum and property of each "mixture" can then be added to the bank and used to develop models through the known correlation/regression approach, e.g. as described in the above mentioned patents.

The method of the invention may be applied from the spectrum of a material to determine at least one physical, chemical, physicochemical and/or rheological property of that material, which may be a product of a chemical or physical or separation process, or which may be a feed to such a process, or the method can be used to determine at least one of said properties of a product of that process from the spectrum of at least one feed to that process, or to determine the yield of at least one product of that process. Each of the feed (or feeds) or products to the process may be a solid liquid or gas preferably at least one feed or product is a liquid.

Thus the method may be used for the physicochemical determination or prediction in relation to at least one feed or product used in or obtained by an industrial process of the refining of oil and/or in petrochemical operations. The process maybe a hydrocarbon conversion or separation process, preferably a reforming or catalytic cracking or hydrotreatment process or distillation or blending. In particular it may be used for determination of at least one property of a feed and/or the prediction and/or determination of at least one property and/or yield of product from a number of different processes such as processes for separating petroleum products such as atmospheric distillation vacuum distillation or separation by distillation, under pressure greater than atmospheric, as well as thermal or catalytic conversion, with or without partial or total hydrogenation, of a petroleum product, such as catalytic cracking e.g. fluid catalytic cracking (FCC), hydrocracking, reforming, isomerization, selective hydrogenation, viscoreduction or alkylation.

Of particular value is the use of the method in blending operations involving the prediction and/or determination of at least one property of a blend of liquid hydrocarbons (optionally with other additives such as alkyl ethers), this method including or not the determination for each constituent of the blend of a blend index for the property considered. In this method as applied to blending, the blend indices can be obtained simply by calculation and without the need for preparation of standard physical mixtures other than those contained in the databank. The blend indices can be combined linearly or non linearly within the fields of stability to determine from the value of this combination a value for at least one property of the blend obtained. The blend may be made by mixing at least 2 of butane, hydrogenated steam-cracked gasoline, isomerate, reformate, MTBE or TAME, FCC derived gasoline. This process may be repeated with numerical addition of other constituents separately to the liquid hydrocarbon base to determine a series of blending indices and then determination from these indices of the properties of the multi constituent blend (see e.g. Ex. 2 hereafter).

Examples of properties that can be determined and/or predicted include the following: for automobile fuels/gasolines, at least one of the Research Octane Number (RON), Motor Octane Number (MON) and/or their arithmetic mean, with or without lead additive and/or the methyl tert, butyl ether or methyl isoamyl ether and/or benzene content:

For automobile fuels/gasolines, at least one of the vapour pressure, density, volatility, distillation curve, e.g. percentage distilled at 70° C. and/or 100° C., oxygen content or benzene or sulphur content, chemical composition and/or gum content e.g. expressed in mg/100 ml, and/or susceptibility to lead (these properties are particularly determined for use in blending operations):

For diesel fuels or gas oils, at least one of the cetane number (e.g. motor measured), cetane index, cloud point, "discharge point", filterability, distillation curve, density e.g. at 15° C., flash point, viscosity e.g. at 40° C., chemical composition, sensitivity to additives and percentage of sulphur;

For distillation products from crude oil e.g. under atmospheric pressure at least one of the density, percentage of sulphur, viscosity at 100° C., distillation curve, paraffin content, residual carbon content or Conradson carbon content, naphtha content, flash point for petrol, cloud point for gas oil e.g. light gas oil and/or viscosity at 100° C. and/or sulphur content for atmospheric residues, and yield for at least one of the cuts, gasoline (bp 38°–95° C.), benzine (bp 95°–149° C.) naphtha bp 149°–175° C., jet fuel bp 175°–232° C., light gas oil bp 232°–342° C., heavy gas oil bp 342°–369° C., and atmospheric residue greater than 369° C.

For at least one of a feed or a product of a process of a catalytic cracking e.g. FCC process, at least one of the density, percentage of sulphur, aniline point, gas oil index, gasoline index, viscosity at 100° C., refractive index at 20° C. and/or 60° C., molecular weight, distillation temperature e.g. 50% distillation temperature, percentage of aromatic carbon, content of total nitrogen and factors characterizing the suitability of the feed for the cracking e.g. KUOP, crackability factor, cokability factor, and yield e.g. of gas, gasoline, gas oil or residue. Thus there may be determined the yields and/or properties of the different products obtained by distillation of the cracked products, such as RON and/or MON, clear or leaded for the gasoline cut and the viscosity at 100° C. for the distillation residue.

For at least one of a product or a feed of a catalytic reforming process, at least one of the density, distillation temperature and/or chemical composition (expressed as a percentage) of saturated linear hydrocarbon, isoparaffins, naphthenes, aromatics and olefins.

For at least one of a product or a feed of a process of hydrogenating gasoline at least one of the density, distillation temperature, RON and/or MON, clear or leaded vapour pressure, volatility, chemical composition (expressed as a percentage) of saturated linear hydrocarbons, isoparaffins, naphthenes, aromatics e.g. benzene, and mono/di substituted benzenes, olefins e.g. cyclic and non cyclic olefins, diolefins, the maleic anhydride index, and yield e.g. of at least one of the products obtained.

The method of the invention may also be used with chemical reactions in which at least one product is a hydrocarbon, and none of the feeds or products contains an element other than carbon or hydrogen. The hydrocarbon which may be gaseous or liquid at 25° C. Such reactions may involve as feed or product at least one olefin or acetylene e.g. linear or branched, aliphatic or cycloaliphatic olefin with an internal or external ethylenic unsaturation, preferably of 2–20 carbons especially 2–8 carbons for alkenes or alkynes (such as ethylene, propylene, butene 1 or 2, isobutene, isopentene) or acetylene, and 5–8 carbons for cycloalkenes e.g. cyclohexene. The feed or product may also be an aromatic hydrocarbon e.g. benzene or naphthalene, optionally substituted by at least one (e.g. 1–3) alkyl or alkenyl group e.g. of 1–20 carbons, such as 1–6 carbons, especially methyl, ethyl or isopropyl; examples are benzene, toluene xylene, cumene and styrene. The feed or product may also be a non aromatic hydrocarbon, e.g. linear or branched aliphatic or cycloaliphatic with e.g. 1–20 or 5–8 carbons respectively, preferably 1–6 carbons and 6 or 7 carbons respectively, examples are methane, ethane, propane, n-butane, isobutane, and cyclohexane. The feed or product may also be a diene, conjugated or unconjugated, aliphatic or cycloaliphatic with e.g. 4–20 carbons or 6–20 carbons respectively; examples are butadiene and isoprene and cyclohexadiene. Examples of the reactions are hydrogenation (e.g. butadiene to butene-1 or 2 or cyclohexene to cyclohexane) dehydrogenation (e.g. ethane to ethylene or ethyl benzene to styrene), isomerisation (e.g. butene-1 or -2 to isobutene, or pentene-1 to isopentene) alkylation (e.g. benzene with ethylene to form ethylbenzene and/or styrene, or isobutene with butane to form iso octane), and cracking.

In addition to the use in petrochemical operations, the method is of wider application and may be applied in the pharmaceutical industry such as the production of pharmaceutically active compounds for use as medicines e.g. by fermentation, and in the perfumery industry for making perfumes and fragances, especially in their blending and control thereof. The method may also be used in the food industry e.g. in brewing to control fermentaion processes, in fermentation to make wine and quality control thereof, and control of food production e.g. sugar and water content in fruit juice and in control of maturing processes for fruits and vegetables. In each case the method may be applied to determine a property of the sample tested or product from that sample e.g. a fermentation or blended product preferably on line and especially with continuous feed back from the results to control the production process.

In each of the above processes the property or yield of a product determined or predicted by the method of the invention can be compared to the desired figure and notice taken of any deviations by adjusting the parameters of the process e.g. proportion or nature of feed(s) and/or temperature/pressure etc to bring the property back to the desired figure. This control of the process, which may be a blending, separation or chemical process, is usually performed with a micro computer which is linked to the spectrometer and also performs the search for the standards Sm. The inline control of the process is very efficient and very fast.

The present invention also provides an apparatus suitable for carrying out the method of the invention comprising an infra red spectrometer and a computer wherein the infra red spectrometer is linked to the computer programmed in such manner that the property or yield may be determined continuously and in real time. The spectrometer is suitable for measuring spectra in the 600–2600 nm wavelength range and can be linked to a signal processing device to allow numerical treatment of the spectrum, preferably by Fourier Transformation. The spectrometer receives at least one signal from a vessel containing product or from a feed or product line. The information obtained can be used as an information vector for the computer which is programmed to determine the property or yield e.g. via calculations on the proximity indices in relation to standards. Conveniently in relation to a process, the computer may be used in a closed loop feedback control system for controlling processing equipment e.g. changing the process parameters in response to variations in the property and/or yield of product from the desired value, from measurement of more than one absorptions in the NIR spectrum of the product and/or feed.

The benefits of invention allow improvements in modelling with the following areas, identification and classification of novel products, simultaneous estimation of all of P properties on a sample without the need for generating P different models, and with the option of automatic upgrading of the model, the method being self learning or adjusting. The method of the invention overcomes the difficulties with the classical regressional approach, in particular avoiding all difficulties with numerical stability of the models, allowing easy and rapid identification and classification of a sample of a product analyzed by spectral recognition and then instant conclusions as to whether the sample is known or unknown, allowing simultaneous determination of many properties and whether the property is simply additive or synergetic in relation to a blend composition; the latter is particularly useful for different blend indices and the indices considered.

The method also allows an extension of the field of application of the method without the need to rewrite the model, apart from the need to integrate the new samples which are inside or outside the previous field of validity of the method. This possibility of automatic learning, which is not possessed by traditional regression techniques, is a decisive advantage in the framework of continuous inline industrial control processes, because it allows the return of the industrial plant operations to the model in a certain and rapid manner in a minimum time and with all the properties considered in the model. In contrast classical regression methods would necessitate the redevelopment of all the models, which is long and laborious without being able to guarantee the result of the new model obtained, because a new validation period is necessary; in addition during the redevelopment of the model any commercial refinery use of the model is very limited. Furthermore, the method of invention allows equally the easy extension to a number of properties, which are simply incorporated into the known bank.

This remarkable possibility is true not only for conventional properties such as physical chemical and/or rheological properties, but also for complex ones (such as octane number). Also it is possible to quantify by the process the response or susceptibility to lead of automobile fuels as well as the response to additives such as nitrates, of fuels used in diesel engines. The methods of the invention equally allow application of the models from one apparatus to another and from one spectral region to another, where conventional regressive method cannot give satisfactory solutions. This apparatus portability is made possible by the fact that the differences between different spectra are the same in one apparatus as another, for the same type of spectrometer being considered (e.g. network scatter, Fourier transform, accousto optical system AOTS, diode array etc). This portability between spectral regions depends on the fact that as the spectral regions are intercorrelated, the relations between the spectra are maintained between one another.

The invention is illustrated in the following Examples in which the Minimal Index is calculated according to the Minimal Index Procedure described above. Mathematically the steps concerned are as follows.

For each couple of standard samples i, j, the Proximity Index $i_{ij}$ is determined from the NIR spectra by use of equation 1, 2, or 3 and the properties are measured. For each Proximity Index is calculated the absolute difference $EP_{ij}$ between the properties of the samples. The Minimal Index for property P is obtained from the average ($EM_pL$) of $EP_{ij}$ for different values of L when L≧ij. Thus the $EM_pL$=1/K$\Sigma\Sigma EP_{ij}$ for each of K samples for which ij≧L.

EMp(L)+tσ(M) is plotted against the proximity index and in addition there is plotted the reproducibility of the standard method at a given level of confidence, as defined in the Minimal Index Procedure above. The intercept of the curve from EMpL and the reproducibility give the upper limit i.e. the Minimal Index.

For the Examples the data is expressed in Tables in a form as shown below in which the data is as follows.

|  | | Absorption | | |
|---|---|---|---|---|
| Weighting | Un-known | Esti-mated | Standard A | Standard B |

Proximity Index

Wavelength λ
$cm^{-1}$     nm
Property l
Property j
Property m

The wavelengths chosen are shown in columns 1 and 2.

Column 3 gives the weight loading associated with each wavelength for the proximity index for the standards; 1 denotes no loading.

Column 4 shows for the unknown sample the absorption at the various wavelengths and at the bottom the properties of that sample determined by standard methods.

Column 5 shows for the unknown sample the estimated values of the properties and the absorptions using the method of the invention based on the properties and absorptions of the chosen standards.

Columns 6, 7 etc show the values of the absorptions and properties for the standards chosen from the bank. Line 2 give the value of the proximity index between the unknown sample and each of the chosen standards.

EXAMPLE 1

Determination of Octane Number and other Properties of a Motor Fuel

The NIR spectra between 4800 and 4000 $cm^{-1}$ of a superfuel 1D and a number of standard superfuels of known properties were measured. The base line was taken at 4780 $cm^{-1}$ though similar results would be obtained with baseline drawn between 2 or more points. The absorbances were normalized.

By the Minimal Index Procedure described above, with use of equation 2 and non weighting of the absorbences the Minimal Index (MI) was calculated to be $1\times10^{-4}$. Following reference to the bank of data on superfuels and use of Procedure 1, 3 standard samples were found with a proximity index with respect to the superfuel of less than M1. The properties of these standards are shown in Table 1. From the properties of the standard samples, octane numbers (RON and MON), vapour pressure (hpa) volatility, percentage distilled at 70° C. and at 100° C., gum content (in mg/ml), and content of sulphur, benzene (vol %) and MTBE were calculated for the superfuel by taking the arithmetic mean of the values for the 3 chosen standards. The estimated results are compared with the measured results.

All the properties were obtained from the single NIR measurement on the unknown superfuel and without any regression calculations, and with an accuracy in agreement with the reproducibilities of the reference methods. Other properties can be determined in a similar way.

EXAMPLE 2

(a) Production of an Unleaded Mixed Fuel from 6 Components

A target SUPER98 superfuel of the properties given in column 3 of Table 2a1, was to be obtained by mixing the remains of a tank of finished gasoline with 5 components, butane, hydrogenated steamcracked gasoline HEN, isomerate ISOM, reformate (REF) and MTBE. NIR absorptions at 4800–4000 $cm^{-1}$ measured with a Fourier Transform spectrometer were measured, with a base line taken at 4780 $cm^{-1}$ and absorbances normalized. Results are in Table 2a1.

Mathematic calculations were done with a computer to mix the spectra and properties of the 6 components to reproduce a finished product.

5% MTBE (on target fuel) (i.e. 4–76% in the final mixture) was "added" mathematically to a spectrum of the target fuel to give a mixture whose NIR spectrum was noted. The Minimal Index was $1\times10^{-4}$ determined as described above from the finished gasoline. 3 standards 2A, 2B and 2C were found with proximity indices with respect to the mixture, without weighting, and hence by averaging the properties of the standards the properties of the mixture were obtained. Table 2a.2 shows the spectrum of the mixture, the 3 standards and the estimation for the mixture as well as the properties of the standards and the estimated figures). The process was repeated with addition of each of the other 4 components to the spectrum of gasoline target.

On the basis of the figures obtained, the blending index for each property was found according to the linear formula $$I^P(mix)=[(1+\alpha)\times P(mix)-P(ref)]/\alpha$$

where $I^P$ (mix) is the blending index for the ingredient in the mixture in relation to property P α is the percentage of ingredient in the mixture P (mix) is the property of the mixture (ingredient+gasoline) added) estimated by the process.

P (ref) is the property of the reference target gasoline.

The blending index for addition of MTBE is shown in Table 2a3.

In order to obey the linearity law here, it is necessary to limit the additions to not more than a quarter of the minimum to maximum range of the constituent studied in the industrial mixtures. However for concentration less than 20% such as for these oxygenated compounds, addition of 5% is acceptable.

The process with MTBE added to the gasoline was repeated with the other 4 components (and on the basis of linearity in the blending as with MTBE) to obtain blending indices for them as well (see Table 2a3). Then with the blending indices for each property for each ingredient, one can calculate the relative volume fractions needed to give the desired properties for the Superfuel 98 and hence the blending order. The 6 components were then mixed in the desired proportions and then properties of the mixture tested and compared to those estimated by the method of the invention from the components present (see Results in Table 2a4). In the estimation of the products and the comparison with the bank of standards, the Minimum Index was $1 \times 10^{-4}$. 3 standards 2D, 2E, 2F were found with suitable proximity indices from which the properties of the superfuel were estimated by averaging as described in Procedure 1. There was good agreement between the properties obtained via the blending order, these measured on the fuel made and those estimated by the method of the invention. The differences are very small and in the area of reproducibility of the standard methods.

EXAMPLE 2b

Production of a 5 component leaded Superfuel mixture

A target superfuel of the SUPER 97 type had with 0.15 g/l of lead tetraethyl and having as specification an RON of 97, an NIR spectrum as in Col 3 of Table 2b1 below and other properties as given in col 3 of Table 2b1 below. There were available 4 components (HEN, 150M, REF and an FCC cat cracker gasoline) and the remains of a tank of finished refined gasoline for making the target fuel. The NIR spectra of these 5 components were measured as in Ex 2. The results are in Table 2b1.

As in Ex. 2a, mathematical calculations were done with a computer to obtain the spectra and properties of 5 components to reproduce a finished product. Proximity indices with respect to standard samples were calculated based on normalized absorbencies which were not weighted. The method of the invention was used to find appropriate standards, using the procedure of artificial mixtures as described in Procedure 3 and equation 8 above in which v was 1 and with a Min. Index of $2 \times 10^{-4}$, the latter having been calculated for standard fuel mixtures as described above. Table 2b2 describes the results of addition of 5% of the FCC gasoline to a reference Super 97 gasoline target as well as the 3 standards 2G, 2H, 2J found by the method of this invention, from which the estimated properties were found. The same procedure was performed with the other components.

The blending indices were found in the same way as for Ex 2a, with the results for FCC gasoline in Table 2b3 and for the other components in the same way. The spectral blending index (for the linear area) is obtained for each property as shown in Table 2b3. A blending order was also calculated, as in Ex 2a, the results being in Table 2b3.

The process of Ex 2a was repeated but with the above components and a Minimal Index of $2 \times 10^{-4}$. The results are in Table 2b4. 3 standards 2K, 2L, 2M were found with appropriate proximity indices, which allowed the properties of the product to be estimated by averaging. Again good agreements is seen between the properties estimated from the blending order and those measured on the product made, and also between the same properties measured and those measured by the process. The differences seen are very small and in the area of reproducibility of the standard methods. Other properties can be obtained in a similar way.

EXAMPLE 3

Determination of cetane index and other properties of a gas oil

The properties of an unknown gas oil 3A were desired. The method of this invention was applied with respect to a bank of known standard gas oils with known NIR spectra. The NIR spectra were obtained by F T spectrometer in the 4800–4000 $cm^{-1}$ region [with 4780 $cm^{-1}$ baseline and were normalized] The proximity indices were calculated on the basis of Equation 2, and the Minimal Index was $2.5 \times 10^{-6}$ (estimated from standard gas oil data as described above). The bank of standards was sufficiently dense for there to be found 2 standards 3B and 3C inside the sphere with proximity index less than $2.5 \times 10^{-6}$. Table 3.1 gives the details of the spectra and properties of the unknown oil A, and the standards and the estimated spectrum and properties, obtained by averaging. All the properties were obtained with an accuracy in agreement with the limits of reproducibility of the reference methods. Other properties can be obtained in a similar way.

EXAMPLE 4

On line prediction, based on NIR spectra on a mixture of crude oils fed to an atmosphere distillation unit, of yields and properties of the different distillation cuts such as gasoline (38°–95° C.) benzine (95°–149° C.) naphtha (149°–175° C., jet fuel (175°–232° C.) light gas oil (232°–242° C.) heavy gas oil (342°–369° C.) and atmospheric residue (bp). 369° C.).

An atmospheric distillation unit in a refinery was fed with a charge 4C which was a mixture in wt % of the following crudes, RUMASHKINO 81%, Iranian Heavy 18%, Iranian light 1%.

Yields of various distillation cuts were desired, the boiling ranges being given above, as well as key properties of each cut as described in Table 4.1, NIR spectra were measured as in Ex 1 on the crude oil. Min. Index was determined from NIR spectra on standard crude oil (as described above) and was $2.6 \times 10^{-6}$. The method of the invention was applied using Procedure 3 and equation 8, in which v was 1, to the bank which was sufficiently dense for 2 standards 4A and 4B to be found with small enough proximity indices. These standards contained (wt %) (for 4A) Romashkino 52%, Iranian Heavy 29%, Arabian Heavy 11%, Kuwait 4%, Arabian light 2% and Iranian light 2%) and (for 4B) Iranian Heavy 78%, Romashkino 21% and Arabian Heavy 1%. The data in Table 4.1 shows the observed properties as well as the yields of the cuts and their properties. The results obtained by this procedure were extremely satisfactory, the differences observed being in accordance with standard methods of measurement. Other properties can be obtained in a similar way.

The yields and properties of the distillation cuts remarkably were obtained directly on the basis of the NIR spectra of the feed and in line without regressional type calculations.

EXAMPLE 5

Determination in line of the properties of a mixture of crude oils

Other properties of the charge mixture of crude oils of Ex 4 were sought, based on the NIR spectra determined as in Ex 4. The method of the invention was applied as in Ex 1 with the Minimal Index in all cases being $2.6 \times 10^{-6}$. Two standard crude petrols 4A and 4B were found in the bank by using Equation 2. The results are shown in Table 5.1. Other properties can be obtained in a similar way.

Here too the method demonstrates its capacity to predict all types of properties without any regression type of calculation requiring fastidious calculations. The results generally, as in the other Example, were in accordance with

15 the results obtained by the reference methods, the deviations being found in the limits of reproducibility of the same methods.

EXAMPLE 6

Determination of the Properties of a feed to a reformer

A feed 6D to a reformer unit was analysed by the method of the invention as described in Example 1 with the NIR spectra recorded at 2000–2500 nm, the absorbancies normalised and not weighted. The NIR spectrum was compared by the method of Procedure 3 and equation 8 (wherein v is 1) with a Minimum Index of $2 \times 10^{-4}$, which had been previously calculated as described above from NIR spectra on standard reformer feeds. Three standards 6A, 6B and 6C from the reference feed bank were found with small enough proximity indices; details of the spectra of the feed and the standards are given in Table 6.1, together with 5 properties estimated for the feed by averaging the corresponding values of those standards. The actual properties of the feed were measured for comparison; the measurements were by traditional methods (gas chromatography and density), the former necessitating laboratory determination for several hours, compared to the present NIR process which gave the same results in a few minutes and on line (real time in the unit) and with better reproducibility.

The process allows the obtaining of a result with remarkable economy while avoiding having to produce 5 regressive models. The differences between the 5 properties as estimated and as measured experimentally are in agreement with the reproducibility of the known reference methods, namely 1.5% for gas chromatography for chemical compositions and 2‰ for density. The method can be equally applied for other properties such as ASTM distillation temperature curve for the feed.

EXAMPLE 7

Determination of the properties of a feed to an FCC unit, as well as the yield and properties of the products obtained The NIR spectrum of the above feed 7D was measured at 4800–4000 m$^{-1}$, with base line at 4780 cm$^{-1}$, normalisation of the spectrum and no weighting. The procedure 3 was used with equation 8, with v=1, and the Min. Index of $2.5 \times 10^{-6}$ the latter having been previously calculated as described above from NIR spectra on standard FCC feeds of known properties.

The properties of the feed charge 7D sought were listed in Table 7.1 and included factors characterising the charge to the FCC unit, such as KUOP, crackability and cokability. The KUOP or Watson factor is defined as $$KUOP = \sqrt[3]{V\theta}/\text{density } 60/60$$

where $\theta$ is boiling point on a Rankin scale (Absolute Fahrenheit scale) and density 60/60 is the density of the feed at 60° F. compared to that of water at 60° F.

The cracking unit operated under the following conditions: riser inlet temperature 250° C., riser outlet temperature 525° C., MHSV (Mass Hourly Space Velocity) 78 kg/h per kg, C/O ratio 6.6, activity of catalyst 65 (in Microactivity Test).

The cracking gave a gasoline cut defined by ASTM distillation with initial point of 38° C. and 90% distilled at 190° C. and a residue defined by ASTM distillation with 10% distilling at 385° C.

16

By application of Procedure 3 to the bank of samples of FCC feeds 2 standards were found namely 7A, 7B and the properties and yields estimated as shown in Table 7.1. The results were all in line with the accuracy based on the reference methods, as well as in line with the properties and yields actually meansured. Other properties of the charge or products can be estimated in a similar way.

EXAMPLE 8

On line determination of properties of the feed to a gasoline Hydrogenation unit The gasolines obtained from steam cracking units have the inconvenience of containing non negligible amounts of unsaturated dienic compounds, which have the effect of inducing and encouraging formation of gums which are undesirable in motor fuel. These gasolines are therefore selectively hydrogenated to eliminate the dienes without at the same time hydrogenating other unsaturated compounds present in the gasoline such as monoolefins and aromatics. The control over these dienes is therefore essential not only for the final quality of the fuel (principly RON and MON) but also for the hydrogen consumption of the hydrogenation unit.

Units for Hydrogenating gasolines from steamcrackers are generally coupled to a downstream distillation unit to separate a gasoline from a light cut (95% distillation by about 75° C.) and one from a heavy cut (initial point about 95° C.), before extraction of the benzene in the core cut and recycle of the extraction residue from that cut called raffinate.

It was desired to determine by the process of the invention the properties of the gasoline from the steam cracker, which was a feed to a gasoline hydrogenation unit. NIR spectra were obtained on the feed on line at 1000–1600 nm using a scatter dispersion spectrometer. The absorbences were normallised, but the data was not weighted for use in Equation 8, in which v was 1 and $i_{min}$ was $2.5 \times 10^{-5}$ (the latter having been determined from NIR spectra on similar feeds of known properties). 5 standards 8A–8E were found in the search using Procedure 3, and the properties of the feed calculated therefrom by averaging were all in agreement with the measured properties of the feed. The results are shown in Table 8.1.

In addition the chemical composition of the feed was obtained with great particularity allowing a distinction to be made for example between cyclic and non cyclic olefins as well as benzene and mono and di substituted aromatics. Equally by the process potential yields were obtained of the distillation cuts after the selective hydrogenation of the gasoline. All the properties were obtained with great accuracy within the limits of the experimental reproducibility for that kind of property.

Other properties can be determined such as Octane Indices for the different cuts or temperatures of ASTM distillation curves for the gasoline.

EXAMPLE 9

Method for use when the density of standards in the bank is insufficient

The MON level for a reformate 9A was sought. The NIR spectrum was measured at 4800–4000 cm$^{-1}$ with a base line at 4780 cm$^{-1}$; the spectra were normalised. With reference to NIR spectra on reformates of known properties the Minimal Index was found by calculation as described above to be $2\times10^{-5}$. The proximity indices of reformate 9A and known standards were determined by Procedure 1. The results were as given in Table 9.1. 5 standards 9B–F were found from the reformate bank with proximity indices low in relation to the reformate 9A, but insufficiently low to be less than Minimal Index, as the density of the bank was too small. It was thus not possible to calculate the properties with the accuracy desired. Procedure 1 using Equation 1 was replaced by Procedure 2 using Equations 4–7, with in Equation 4 values of Cj between −0.3 and +1.3, in order to increase the density of "standards" in the bank by providing new synthetic mixtures.

Tables 9.2 and 9.3 show the results obtained, showing in Column 3 the absorbancies and properties for the "standards" (MC1, MC2) obtained by this densification, and with small enough proximity indices. Col. 4 and subsequent columns give the absorbances properties of the standards 9B, 9D and 9G in the reformate bank used to generate the new "standards". Line 2 in these Tables show for each standard the fraction retained in the mixture to generate the new "standards" This fraction can be negative, but comprises between −0.3 (or −0.4) and +1.3 (in Eq. 4).

Using the data on MC1 and MC2 as "standards", the properties of the reformate 9A were calculated by averaging (as shown in Table 9.4). The calculated MON of reformate 9A accords well with the experimentally measured figure, and is inside the limits of reproducibility of the standard method. The process can be used in a similar way for other properties.

The method of the invention equally allows immediate automatic upgrading of the bank by automatic integration of the new samples. The process with the proximity indices allows consideration as a standard of all the novel "standards" introduced into the bank. This property is remarkable because it allows very rapid determination of properties in the case of novel products not recognised in the bank and then the gaining of precious time in the adjustment of operating conditions for the manufacturing unit.

Table 9.5 shows that a novel "sample" measured immediately after incorporation of the above unrecognised sample 9A in the databank, now used as a standard, is recognised and is perfectly calculated for the totality of its properties and without any modification nor intervention on the used models. It is important to note the superiority of the procedure over classical regressional models. The latter are incapable of predicting properties of samples not included within their application range or predict them with a non acceptable error, and therefore would need to be reactivated by the necessity to remake the model (one for each property) and this without guarantee of success, and with the commercial plant functioning blind during the recalibration period.

TABLE 1.1

Determination of Octane Indices and other Properties in an automobile fuel

| Proximity Index Wavelength | | | 1D | 1D Estimated 0,0000275 | 1A 0,00006 | 1B 0,00007 | 1C 0,00009 |
|---|---|---|---|---|---|---|---|
| λ (cm − 1) | λ (nm) | Weighting | Measured | 26 | 7452 | 2577 | 6807 |
| 4720 | 2119 | 1 | 0,002103 1 | 0,0021115 | 0,00219 85 | 0,00206 78 | 0,00206 83 |
| 4670 | 2141 | 1 | 0,01696 | 0,016887 | 0,01702 9 | 0,01683 1 | 0,01680 1 |
| 4640 | 2155 | 1 | 0,016172 | 0,016464 | 0,01717 1 | 0,01569 5 | 0,01652 7 |
| 4615 | 2167 | 1 | 0,023426 | 0,022955 | 0,02267 1 | 0,02276 5 | 0,02342 9 |
| 4585 | 2181 | 1 | 0,014407 | 0,014379 | 0,01424 1 | 0,01486 3 | 0,01403 4 |
| 4485 | 2230 | 1 | 0,011377 | 0,011472 | 0,01151 6 | 0,01178 8 | 0,01111 2 |
| 4460 | 2242 | 1 | 0,015794 | 0,015825 | 0,01571 8 | 0,01533 1 | 0,01642 8 |
| 4385 | 2281 | 1 | 0,092392 | 0,090762 | 0,09071 | 0,09287 4 | 0,08870 1 |
| 4332 | 2308 | 1 | 0,127 | 0,12402 | 0,12292 | 0,1241 | 0,12505 |
| 4305 | 2323 | 1 | 0,10482 | 0,10678 | 0,1021 | 0,10946 | 0,10879 |
| 4260 | 2347 | 1 | 0,10001 | 0,099412 | 0,09862 1 | 0,09552 4 | 0,10409 |
| 4210 | 2375 | 1 | 0,065489 | 0,06726 | 0,06746 3 | 0,06666 4 | 0,06765 |
| 4170 | 2398 | 1 | 0,063954 | 0,06449 | 0,06643 4 | 0,06449 1 | 0,06254 6 |
| 4135 | 2418 | 1 | 0,066992 | 0,067348 | 0,06552 3 | 0,06707 5 | 0,06944 5 |
| 4105 | 2436 | 1 | 0,066911 | 0,066291 | 0,06655 1 | 0,06498 7 | 0,06733 6 |
| 4060 | 2463 | 1 | 0,10946 | 0,11196 | 0,11349 | 0,11337 | 0,10903 |
| 4040 | 2475 | 1 | 0,10273 | 0,10157 | 0,10564 | 0,10211 | 0,09695 9 |
| RON clear | | | | 99,4 | 99,2 | 99 | 99,3 | 99,4 |
| MON clear | | | | 88,4 | 88,2 | 88 | 88,1 | 88,4 |
| TV hpa | | | | 700 | 705,0 | 710 | 715 | 690 |
| Volatility | | | | 980 | 975,0 | 983 | 967 | 975 |
| % Dist 100° C. | | | | 58 | 54,7 | 54 | 58 | 52 |
| % Dist 70° C. | | | | | 36,8 | 37 | 39 | 37 | 35 |

TABLE 1.1-continued

Determination of Octane Indices and other Properties in an automobile fuel

| Proximity Index Wavelength | | | 1D | 1D Estimated 0,0000275 | 1A 0,00006 | 1B 0,00007 | 1C 0,00009 |
|---|---|---|---|---|---|---|---|
| λ (cm − 1) | λ (nm) | Weighting | Measured | 26 | 7452 | 2577 | 6807 |
| Resin | | | 1.4 | 1,6 | 1,2 | 1,7 | 1,8 |
| % Sulphur | | | 0.038 | 0,043 | 0,035 | 0,045. | 0,048 |
| Benzene % Vol | | | 0.7 | 0,8 | 0,6 | 0,85 | 0,9 |
| MTBE | | | 5.6 | 5,8 | 4,7 | 6,3 | 6,5 |

TABLE 2a.1

NIR Spectra of Unleaded mixed fuel and base fuel and additives

| λ (cm − 1) | λ (nm) | SUPER FUEL | BASE FUEL | BUTANE | HEN | ISOM | MTBE | REF |
|---|---|---|---|---|---|---|---|---|
| 4720 | 2119 | 0,00138 33 | 0,00132 86 | 0,00036 614 | 0,00487 46 | 0,00045 176 | 0,00039 505 | 0,00178 99 |
| 4670 | 2141 | 0,01540 1 | 0,01569 8 | 0,00059 139 | 0,03592 9 | 0,00181 07 | 0,00079 685 | 0,02742 |
| 4640 | 2155 | 0,01445 8 | 0,01478 6 | 0,00154 83 | 0,03355 54 | 0,00208 07 | 0,00199 1 | 0,02658 |
| 4615 | 2167 | 0,02162 9 | 0,02193 22 | 0,00243 67 | 0,04847 45 | 0,00337 3 | 0,00336 | 0,03561 |
| 4585 | 2181 | 0,01317 3 | 0,01355 6 | 0,00390 46 2 | 0,02682 92 | 0,00324 56 | 0,00433 7 | 0,02632 |
| 4485 | 2230 | 0,01069 9 | 0,01070 5 | 0,01376 6 | 0,01651 73 | 0,00575 1 | 0,01324 2 | 0,01271 |
| 4460 | 2242 | 0,01531 8 | 0,01564 6 | 0,01671 7 | 0,01885 8 | 0,01010 8 | 0,02791 1 | 0,0181 |
| 4385 | 2281 | 0,09402 3 | 0,09463 8 | 0,10437 | 0,08112 5 | 0,09525 5 | 0,13276 | 0,08467 6 |
| 4332 | 2308 | 0,12974 | 0,13083 | 0,14701 | 0,09487 6 | 0,1474 | 0,18122 | 0,11291 |
| 4305 | 2323 | 0,10626 | 0,10476 | 0,12279 | 0,09342 5 | 0,11981 | 0,06388 5 | 0,10927 |
| 4260 | 2347 | 0,10094 1 | 0,09888 | 0,11439 | 0,08813 3 | 0,11705 | 0,07465 7 | 0,09048 7 |
| 4210 | 2375 | 0,06567 2 | 0,06590 2 | 0,07431 3 | 0,05429 5 | 0,07231 6 | 0,09115 2 | 0,05800 7 |
| 4170 | 2398 | 0,06528 9 | 0,06506 3 | 0,05780 5 | 0,04981 1 | 0,07479 7 | 0,09572 5 | 0,05451 |
| 4135 | 2418 | 0,06914 7 | 0,06866 4 | 0,07986 2 | 0,04623 5 | 0,08584 7 | 0,08344 8 | 0,04925 6 |
| 4105 | 2436 | 0,06864 1 | 0,06770 2 | 0,08969 7 | 0,05082 6 | 0,08208 2 | 0,06768 | 0,05322 9 |
| 4060 | 2463 | 0,10677 | 0,10794 | 0,0875 | 0,12437 | 0,09998 | 0,07699 | 0,12989 |
| 4040 | 2475 | 0,10145 | 0,10197 | 0,08367 4 | 0,13189 4 | 0,07952 | 0,08123 5 | 0,10917 |
| RON clear | | 99,1 | | | | | | |
| MON clear | | 88,2 | | | | | | |
| Vapour Pressure | | 731,74 | | | | | | |
| Volatilite | | 985 | | | | | | |
| % Dist 100° C. | | 49,93 | | | | | | |
| % Dist 70° C. | | 34,4 | | | | | | |

TABLE 2a.2

Effect of addition of MTBE on the Super Fuel

| Proximity Index 80 (cm − 1) | λ (nm) | Weighting | Mixture + 5% MTBE Exp. | Estimated 0,0000190 69 | 2A 0,00004 957 | 2B 0,00006 0618 | 2C 0,00006 8613 |
|---|---|---|---|---|---|---|---|
| 4720 | 2119 | 1 | 0,00133 62 | 0,0012761 | 0,00127 48 | 0,00126 91 | 0,00128 45 |

TABLE 2a.2-continued

Effect of addition of MTBE on the Super Fuel

| Proximity Index 80 (cm − 1) | λ (nm) | Weighting | Mixture + 5% MTBE Exp. | Estimated 0,0000190 69 | 2A 0,00004 957 | 2B 0,00006 0618 | 2C 0,00006 8613 |
|---|---|---|---|---|---|---|---|
| 4670 | 2141 | 1 | 0,014705 | 0,014562 | 0,014384 | 0,014083 | 0,015218 |
| 4640 | 2155 | 1 | 0,013864 | 0,013804 | 0,014523 | 0,013567 | 0,013323 |
| 4615 | 2167 | 1 | 0,020759 | 0,02143 | 0,021489 | 0,021104 | 0,021698 |
| 4585 | 2151 | 1 | 0,012752 | 0,01255 | 0,012204 | 0,01312 | 0,012327 |
| 4485 | 2230 | 1 | 0,01082 | 0,010514 | 0,01041 | 0,01042 | 0,010712 |
| 4460 | 2242 | 1 | 0,015917 | 0,015584 | 0,016158 | 0,015226 | 0,015368 |
| 4385 | 2281 | 1 | 0,095868 | 0,096666 | 0,096107 | 0,09918 | 0,094711 |
| 4332 | 2308 | 1 | 0,13219 | 0,13256 | 0,1298 | 0,12971 | 0,13817 |
| 4305 | 2323 | 1 | 0,10425 | 0,10443 | 0,10689 | 0,10497 | 0,10142 |
| 4260 | 2347 | 1 | 0,099691 | 0,10039 | 0,10436 | 0,098324 | 0,098495 |
| 4210 | 2375 | 1 | 0,066885 | 0,066455 | 0,066544 | 0,065782 | 0,067039 |
| 4170 | 2398 | 1 | 0,066738 | 0,067485 | 0,065091 | 0,069061 | 0,068303 |
| 4135 | 2418 | 1 | 0,069828 | 0,071186 | 0,069457 | 0,07235 | 0,07175 |
| 4105 | 2436 | 1 | 0,068596 | 0,066773 | 0,065937 | 0,06768 | 0,0667 |
| 4060 | 2463 | 1 | 0,10535 | 0,10236 | 0,10385 | 0,101 | 0,10222 |
| 4040 | 2475 | 1 Reference SUPER98 | 0,10049 | 0,10197 | 0,10152 | 0,10314 | 0,10126 |
| RON clear | | | 99,1 | 99,6 | 99,7 | 99,5 | 99,5 |
| MON clear | | | 88,2 | 88,7 | 88,9 | 88,5 | 88,7 |
| Vapour Pressure | | | 731,74 | 718,8 | 711,2 | 720,0 | 725,2 |
| Volatility | | | 985 | 972,3 | 970,0 | 979,2 | 967,6 |
| % Dist 100° C. | | | 49,93 | 52,3 | 52,0 | 54,0 | 50,8 |
| % Dist 70° C. | | | 34,4 | 35,8 | 36,3 | 35,4 | 35,8 |

TABLE 2a.3

Blending Indices and Blending Order

| (blending order) | Base Fuel | Butane | HEN | ISOM | MTBE | REF |
|---|---|---|---|---|---|---|
| Volume Fraction | | 19,30% | 4,10% | 31,70% | 32,10% | 5,60% | 7,2% |
| RON clear | 99,4 | 100,2 | 97,5 | 103,6 | 93,0 | 109,6 | 100,7 |
| MON clear | 88,2 | 88,0 | 88,5 | 88,0 | 86,7 | 98,7 | 88,42 |
| Vapour Pressure | 709,1 | 767,0 | 4700,0 | 98,7 | 923,0 | 460 | 208,2 |
| Volatility | 972,4 | 975,0 | 5000,0 | 212,0 | 1430,0 | 718,3 | 177,3 |
| % Dist 100° C. | 54,9 | 50,2 | 200,0 | −5,0 | 97,5 | 99,7 | 24 |
| % Dist 70° C. | 37,8 | 31,3 | 142,8 | −12,9 | 84,2 | 63,8 | −8,3 |

TABLE 2a.4

Comparison of the result obtained via the blending order and those of the product obtained

| Proximity Index λ (cm − 1) | λ (nm) | Weight | Made | Estimated 0,0000275 26 | 2D 0,00006 7452 | 2E 0,00007 2577 | 2F 0,00009 6807 |
|---|---|---|---|---|---|---|---|
| 4720 | 2119 | 1 | 0,0021031 | 0,0021115 | 0,0021985 | 0,0020678 | 0,0020683 |
| 4670 | 2141 | 1 | 0,01696 | 0,016887 | 0,017029 | 9,016831 | 0,016801 |
| 4640 | 2155 | 1 | 0,016172 | 0,016464 | 0,017171 | 0,015695 | 0,016527 |
| 4615 | 2167 | 1 | 0,023426 | 0,022955 | 0,022671 | 0,022765 | 0,023429 |
| 4585 | 2181 | 1 | 0,014407 | 0,014379 | 0,014241 | 0,014863 | 0,014034 |
| 4485 | 2230 | 1 | 0,011377 | 0,011472 | 0,011516 | 0,011788 | 0,011112 |
| 4460 | 2242 | 1 | 0,015794 | 0,015825 | 0,015718 | 0,015331 | 0,016428 |
| 4385 | 2281 | 1 | 0,092392 | 0,090762 | 0,09071 | 0,092874 | 0,088701 |
| 4332 | 2308 | 1 | 0,127 | 0,12402 | 0,12292 | 0,1241 | 0,12505 |
| 4305 | 2323 | 1 | 0,10482 | 0,10678 | 0,1021 | 0,10946 | 0,10879 |
| 4260 | 2347 | 1 | 0,10001 | 0,099412 | 0,098621 | 0,095524 | 0,10409 |
| 4210 | 2375 | 1 | 0,065489 | 0,06726 | 0,067463 | 0,066664 | 0,067653 |
| 4170 | 2398 | 1 | 0,063954 | 0,06449 | 0,066434 | 0,064491 | 0,062546 |
| 4135 | 2418 | 1 | 0,066992 | 0,067348 | 0,06552 | 0,06707 | 0,06944 |
| 4105 | 2436 | 1 | 0,066911 | 0,066291 | 0,066551 | 0,064987 | 0,067336 |
| 4060 | 2463 | 1 | 0,10946 | 0,11196 | 0,11349 | 0,11337 | 0,10903 |
| 4040 | 2475 | 1 | 0,10273 | 0,10157 | 0,10564 | 0,10211 | 0,09695 |
| | (blending order) | | Measured standards | | | | |
| RON clear | 99,4 | | 99,4 | 99,2 | 99 | 99,3 | 99,4 |
| MON clear | 88,2 | | 88,4 | 88,2 | 88 | 88,1 | 88,4 |
| Vapour Pressure | 709,1 | | 700 | 705,0 | 710 | 715 | 690 |
| Volatility | 972,4 | | 980 | 975,0 | 983 | 967 | 975 |
| % Dist 100° C. | 54,9 | | 58 | 54,7 | 54 58 | 52 | |
| % Dist 70° C. | 37,8 | | 36,8 | 37 | 39 | 37 | 35 |

TABLE 2b.1

NMR spectrum of Target Super Fuel, and base stocks available

| λ (cm − 1) | λ (nm) | Target | Gasoline | FCC | HEN | ISOM | REF |
|---|---|---|---|---|---|---|---|
| 4720 | 2119 | 0,0014234 | 0,0012695 | 0,0029238 | 0,0045838 | 0,0004093 | 0,0016567 |
| 4670 | 2141 | 0,0092828 | 0,0090594 | 0,0059667 | 0,03701 | 0,0020427 | 0,0244449 |
| 4640 | 2155 | 0,0092599 | 0,0090802 | 0,0068228 | 0,0338645 | 0,0021988 | 0,02384 |
| 4615 | 2167 | 0,0132326 | 0,012989 | 0,0092342 | 0,046361 | 0,0035967 | 0,032231 |
| 4585 | 2181 | 0,0098247 | 0,0096662 | 0,0077879 | 0,028857 | 0,0033395 | 0,023754 |
| 4485 | 2230 | 0,0107727 | 0,010379 | 0,014512 | 0,015486 | 0,0058411 | 0,012233 |
| 4460 | 2242 | 0,0144099 | 0,014075 | 0,016828 | 0,018119 | 0,0102 | 0,017515 |
| 4385 | 2281 | 0,0933259 | 0,093268 | 0,095498 | 0,078888 | 0,095201 | 0,085595 |
| 4332 | 2308 | 0,14045 | 0,1408 | 0,1543 | 0,09269 | 0,14681 | 0,11852 |
| 4305 | 2323 | 0,12096 | 0,12085 | 0,13213 | 0,09168 | 0,11947 | 0,11078 |
| 4260 | 2347 | 0,11073 | 0,11062 | 0,11559 | 0,086428 | 0,11763 | 0,093562 |
| 4210 | 2375 | 0,06891 | 0,069012 | 0,07340 | 0,05286 | 0,07213 | 0,06046 |

TABLE 2b.1-continued

NMR spectrum of Target Super Fuel, and base stocks available

| λ (cm − 1) | λ (nm) | Target | Gasoline | FCC | HEN | ISOM | REF |
|---|---|---|---|---|---|---|---|
| | | 3 | | 6 | 1 | 6 | 1 |
| 4170 | 2398 | 0,06968 | 0,069948 | 0,07379 8 | 0,04902 2 | 0,07519 1 | 0,05775 |
| 4135 | 2418 | 0,07122 7 | 0,071736 | 0,06714 3 | 0,04547 7 | 0,08547 1 | 0,05259 |
| 4105 | 2436 | 0,07000 3 | 0,070819 | 0,06500 3 | 0,05096 3 | 0,08220 3 | 0,05617 6 |
| 4060 | 2463 | 0,10201 | 0,10186 | 0,08935 7 | 0,13909 | 0,09970 5 | 0,1243 |
| 4040 | 2475 | 0,08448 9 | 0,08458 | 0,0697 | 0,1286 | 0,07938 1 | 0,10458 |
| RON clear | | 97,9 | | | | | |
| MON clear | | 86,2 | | | | | |
| Vapour Pressure | | 596 | | | | | |
| Volatility | | 905,4 | | | | | |
| % Dist 100° C. | | 62,54 | | | | | |
| % Dist 70° C. | | 42,24 | | | | | |

TABLE 2b.2

Effect of addition of 5% FCC gasoline on Super 97 Product

| Proximity Index Wavelength | | | Mixture | | | | |
|---|---|---|---|---|---|---|---|
| | | | | Estimated | 2G | 2H | 2J |
| λ (cm − 1) | λ (nm) | Weight | Actual | 3.41E-05 | 5.77E-05 | 6.53E-05 | 7.88E-05 |
| 4720 | 2119 | 1 | 0.001495 | 0.001416 | 0.001411 | 0.001414 | 0.001421 |
| 4670 | 2141 | 1 | 0.009125 | 0.008837 | 0.008658 | 0.008768 | 0.009085 |
| 4640 | 2155 | 1 | 0.009144 | 0.008948 | 0.009016 | 0.008955 | 0.008874 |
| 4615 | 2167 | 1 | 0.013045 | 0.012691 | 0.012631 | 0.013035 | 0.012407 |
| 4585 | 2181 | 1 | 0.009728 | 0.009605 | 0.009454 | 0.009682 | 0.009679 |
| 4485 | 2230 | 1 | 0.010955 | 0.010851 | 0.010639 | 0.010909 | 0.011005 |
| 4460 | 2242 | 1 | 0.014524 | 0.014847 | 0.014877 | 0.014917 | 0.014754 |
| 4385 | 2281 | 1 | 0.093432 | 0.094816 | 0.094259 | 0.096722 | 0.093466 |
| 4332 | 2308 | 1 | 0.14111 | 0.14368 | 0.14703 | 0.13759 | 0.1464 |
| 4305 | 2323 | 1 | 0.12149 | 0.12506 | 0.12261 | 0.12658 | 0.12598 |
| 4260 | 2347 | 1 | 0.11096 | 0.11021 | 0.11119 | 0.11141 | 0.10805 |
| 4210 | 2375 | 1 | 0.069127 | 0.06648 | 0.066676 | 0.065499 | 0.067266 |
| 4170 | 2398 | 1 | 0.069879 | 0.068946 | 0.067881 | 0.069493 | 0.069464 |
| 4135 | 2418 | 1 | 0.071032 | 0.070704 | 0.069102 | 0.072032 | 0.070979 |
| 4105 | 2436 | 1 | 0.069765 | 0.069612 | 0.071611 | 0.069153 | 0.068074 |
| 4060 | 2463 | 1 | 0.1014 | 0.1015 | 0.10061 | 0.101 | 0.10289 |
| 4040 | 2475 | 1 | 0.083785 | 0.081801 | 0.082343 | 0.082854 | 0.080207 |
| | | Reference SUPER97 | | | | | |
| RON clear | | 97,9 | | 97.6 | 97.7 | 97.5 | 97.6 |
| MON clear | | 86,2 | | 85.9 | 86.1 | 85.7 | 85.9 |
| Vapour Pressure | | 596 | | 586.1 | 590.0 | 584.2 | 584.2 |
| Volatility | | 905,4 | | 892.2 | 901.0 | 887.5 | 888.0 |

TABLE 2b.2-continued

| Proximity Index | | | Mixture | | | | |
|---|---|---|---|---|---|---|---|
| Wavelength | | | | Estimated | 2G | 2H | 2J |
| $\lambda$ (cm − 1) | $\lambda$ (nm) | Weight | Actual | 3.41E-05 | 5.77E-05 | 6.53E-05 | 7.88E-05 |
| % Dist 100° C. | | 62,54 | | 62.3 | 62.8 | 62.6 | 61.4 |
| % Dist 70° C. | | 42,24 | | 41.7 | 42.5 | 41.7 | 40.9 |

In this Table 3.41E-05 means $3.41 \times 10^{-5}$

TABLE 2b.3

| | Blending Indices and Blending order | | | | | |
|---|---|---|---|---|---|---|
| Volume Fraction | (blending order) | Gasoline 12,93% | FCC 31,85% | HEN 8,46% | ISOM 37,55% | REF 9,20% |
| RON clear | 97.7 | 97.9 | 91.6 | 101.1 | 101.5 | 100 |
| MON clear | 86.3 | 86.4 | 79.9 | 83.5 | 92 | 87.9 |
| Vapour Pressure | 589.9 | 648.0 | 388.1 | 137.7 | 930.0 | 235.0 |
| Volatility | 952.7 | 968.5 | 628.2 | 274.2 | 1559.0 | 204.7 |
| % Dist 100° C. | 65.5 | 63.2 | 57.5 | 6.3 | 96.0 | 26.4 |
| % Dist 70° C. | 45.4 | 43.1 | 30.9 | −10.7 | 83.3 | −4.3 |

TABLE 2b.4

| Comparison between the results from the blending order and the product | | | | | | | |
|---|---|---|---|---|---|---|---|
| Proximity | | | Product | | | 2L | 2M |
| Index $\lambda$ (cm − 1) | $\lambda$ (nm) | Weight | Measured | Estimated 8.41E-05 | 2K 5.36E-05 | 0.000159 | 0.00199 |
| 4720 | 2119 | 1 | 0.001742 | 0.001809 | 0.001775 | 0.001851 | 0.001802 |
| 4670 | 2141 | 1 | 0.009508 | 0.009166 | 0.009131 | 0.009262 | 0.009104 |
| 4640 | 2155 | 1 | 0.008698 | 0.00926 | 0.009326 | 0.009695 | 0.008759 |
| 4615 | 2167 | 1 | 0.012758 | 0.013206 | 0.012772 | 0.013574 | 0.01327 |
| 4585 | 2181 | 1 | 0.009725 | 0.009549 | 0.009242 | 0.009921 | 0.009484 |
| 4485 | 2230 | 1 | 0.010459 | 0.010438 | 0.010486 | 0.010336 | 0.010493 |
| 4460 | 2242 | 1 | 0.014142 | 0.014252 | 0.014878 | 0.013896 | 0.013982 |
| 4385 | 2281 | 1 | 0.090899 | 0.093317 | 0.092897 | 0.09338 | 0.093676 |
| 4332 | 2308 | 1 | 0.13685 | 0.13974 | 0.13652 | 0.13589 | 0.14683 |
| 4305 | 2323 | 1 | 0.11596 | 0.12103 | 0.1195 | 0.1248 | 0.11879 |
| 4260 | 2347 | 1 | 0.11499 | 0.1128 | 0.11271 | 0.11216 | 0.11352 |
| 4210 | 2375 | 1 | 0.071524 | 0.068713 | 0.071255 | 0.068318 | 0.066566 |
| 4170 | 2398 | 1 | 0.070662 | 0.070304 | 0.069855 | 0.069388 | 0.071669 |
| 4135 | 2418 | 1 | 0.072077 | 0.071069 | 0.070001 | 0.07464 | 0.068566 |
| 4105 | 2436 | 1 | 0.069448 | 0.071756 | 0.073371 | 0.071076 | 0.070822 |
| 4060 | 2463 | 1 | 0.10444 | 0.10095 | 0.10163 | 0.098515 | 0.10269 |

TABLE 2b.4-continued

Comparison between the results from the blending order and the product

| 4040 | 2475 | 1 | 0.086116 | 0.08264 | 0.084647 | 0.083297 | 0.079975 |
|------|------|---|----------|---------|----------|----------|----------|

| | (blending order) | Measured standards | | | | |
|---|---|---|---|---|---|---|
| RON clear | 97.7 | 97.5 | 97.7 | 97.8 | 97.5 | 97.7 |
| MON clear | 86.3 | 86.4 | 86.2 | 86 | 86.1 | 86.5 |
| Vapour Pressure | 589.9 | 595 | 598.0 | 596 | 600 | 598 |
| Volatility | 952.7 | 949 | 956.7 | 955 | 960 | 955 |
| % Dist 100° C. | 65.5 | 62 | 63.0 | 66 | 63 | 60 |
| % Dist 70° C. | 45.4 | 47 | 44.2 | 42 | 46.5 | 44 |

TABLE 3.1

Determination of cetane index and other properties of a gas oil

| | Proximity | | Gas Oil A | | | |
|---|---|---|---|---|---|---|
| $\lambda$ (cm − 1) | Index $\lambda$ (nm) | Weight | Measured | Estimated 1,71E-06 | 3B 1,39E-06 | 3C 2,23E-06 |
| 4720 | 2118,6 | 1 | 0,000120383 | 0,000126618 | 0,000139825 | 0,000113411 |
| 4672 | 2140,4 | 1 | 0,001962853 | 0,002013913 | 0,002015876 | 0,002011949 |
| 4640 | 2155,2 | 1 | 0,003434747 | 0,003415109 | 0,003438675 | 0,003391543 |
| 4616 | 2166,4 | 1 | 0,004544314 | 0,004490799 | 0,004476561 | 0,004505037 |
| 4584 | 2181,5 | 1 | 0,004729896 | 0,004675 4 | 0,00463465 | 0,004716149 |
| 4484 | 2230,2 | 1 | 0,007119883 | 0,006932337 | 0,006908771 | 0,006955903 |
| 4460 | 2242,2 | 1 | 0,010349409 | 0,010133388 | 0,010064653 | 0,010202122 |
| 4384 | 2281 | 1 | 0,074606084 | 0,074925207 | 0,074930117 | 0,074920298 |
| 4332 | 2308,4 | 1 | 0,158677852 | 0,157745031 | 0,15799051 | 0,157499551 |
| 4304 | 2323,4 | 1 | 0,101824835 | 0,102266697 | 0,102217602 | 0,102315793 |
| 4260 | 2347,4 | 1 | 0,131871507 | 0,131331453 | 0,131380548 | 0,131282357 |
| 4208 | 2376,4 | 1 | 0,088627865 | 0,088637684 | 0,08855913 | 0,088716237 |
| 4168 | 2399,2 | 1 | 0,092899205 | 0,093012126 | 0,093105408 | 0,01092918844 |
| 4132 | 2420,1 | 1 | 0,084503812 | 0,0847591 1 | 0,084827844 | 0,084690376 |
| 4104 | 2436,6 | 1 | 0,081106377 | 0,08129781 51 | 0,081361676 | 0,081234027 |
| 4060 | 2463,1 | 1 | 0,08642837 | 0,0864872 85 | 0,086487285 | 0,086487285 |
| 4040 | 2475,2 | 1 | 0,067192608 | 0,0674037 2 | 0,067418449 | 0,067388991 |
| Cetane Index | | | 52 | 52,5 | 53,3 | 51,7 |
| Cetane Number | | | 55,3 | 52,75 | 52,1 | 53,4 |
| Density 15° C. | | | 0,8434 | 0,84085 | 0,8385 | 0,8432 |
| Flash Point | | | 62 | 57,5 | 60 | 55 |
| % Sulphur | | | 0,29 | 0,25 | 0,23 | 0,27 |
| Cloud Point | | | 5,1 | 5,5 | 5 | 6 |
| Filterability | | | 1 | 0,5 | 1 | 0 |
| Viscosity 40° C. | | | 3,1 | 3,7 | 3,7 | 3,7 |

TABLE 4.1

Determination of yields and properties of cuts from distillation of mixture of crude feed oils

| | Proximity | | Charse 4C | | 4A | 4B |
|---|---|---|---|---|---|---|
| λ (cm-1) | Index λ (nm) | Weight | Measured | Estimated 9,98E-07 | 1,21E-06 | 1,33E-06 |
| 4672 | 2140,4 | 1 | 0,001777942 | 0,001748627 | 0,001771733 | 0,00172552 |
| 4640 | 2155,2 | 1 | 0,003139917 | 0,003211964 | 0,003256211 | 0,003167717 |
| 4616 | 2166,4 | 1 | 0,00377911 | 0,00327795 | 0,003835639 | 0,003819952 |
| 4584 | 2181,5 | 1 | 0,003794844 | 0,003797791 | 0,003829737 | 0,003765845 |
| 4484 | 2230,2 | 1 | 0,006094959 | 0,00614454 | 0,006272386 | 0,006016694 |
| 4460 | 2242,2 | 1 | 0,009258476 | 0,009155818 | 0,009276757 | 0,009034879 |
| 4384 | 2281 | 1 | 0,078089814 | 0,077898738 | 0,077667019 | 0,078130457 |
| 4332 | 2308,4 | 1 | 0,15773336 | 0,157794497 | 0,157793411 | 0,157795584 |
| 4304 | 2323,4 | 1 | 0,104631107 | 0,1045241 | 0,104179066 | 0,104869135 |
| 4260 | 2347,4 | 1 | 0,130690546 | 0,130249322 | 0,130445176 | 0,130053468 |
| 4208 | 2376,4 | 1 | 0,087815393 | 0,087751054 | 0,087838988 | 0,08766312 |
| 4172 | 2396,9 | 1 | 0,091208037 | 0,090879399 | 0,090878774 | 0,090880025 |
| 4132 | 2420,1 | 1 | 0.084648925 | 0,084706329 | 0,08465164 | 0,084761019 |
| 4104 | 2436,6 | 1 | 0,0824855 | 0,082364989 | 0,082389016 | 0,082340962 |
| 4060 | 2463,1 | 1 | 0,087068028 | 0,087578898 | 0,0874755 | 0,087682795 |
| 4040 | 2475,2 | 1 | 0.067784043 | 0,068366138 | 0,068439449 | 0,068292827 |
| Density 15° C. | | | 0,8663 | 0,86555 | 0,8646 | 0,8665 |
| % Gasoline | | | 7,4 | 7,4 | 7,4 | 7,4 |
| % Benzine | | | 7,6 | 7,2 | 7,3 | 7,2 |
| % Naphta | | | 4,3 | 4,5 | 4,5 | 4,5 |
| % Petrol | | | 8,5 | 8,5 | 8,6 | 8,4 |
| % light gas oil LGO | | | 18,9 | 18,8 | 19,2 | 18,5 |
| % Heavy gas oil | | | 4,5 | 4,5 | 4,6 | 4,4 |
| % Residue RAT | | | 49 | 49,2 | 48,6 | 49,8 |
| % Paraffines Naphta | | | 52,2 | 52,1 | 53,1 | 51,2 |
| Flash Point Petrol | | | 59,2 | 59,5 | 59,8 | 59,3 |
| Cloud point LGO | | | −8,1 | −8,1 | −8,8 | −7,5 |
| % Sulphur RAT | | | 2,8 | 2,8 | 2,8 | 2,9 |
| Viscosity 100° C. RAT | | | 53,16 | 52,72 | 48,53 | 56,91 |

TABLE 5.1

On line determination of properties of a mixture of crude oils

| | Proximity | | Mixture 4C | | 4A | 4B |
|---|---|---|---|---|---|---|
| λ (cm-1) | Index λ (nm) | Weight | Measured | Estimated 1,04E-06 | 1,27E-06 | 1,35E-06 |
| 4672 | 2140,4 | 1 | 0,001777942 | 0,00174849 | 0,001771058 | 0,00172484 |
| 4640 | 2155,2 | 1 | 0,003139917 | 0,0032112 | 0,003254971 | 0,003166468 |
| 4616 | 2166,4 | 1 | 0,00377911 | 0,0032712 | 0,003834179 | 0,003818445 |
| 4584 | 2181,5 | 1 | 0,003794844 | 0,00379719 | 0,003828279 | 0,00376436 |
| 4484 | 2230,2 | 1 | 0,006094959 | 0,00614461 | 0,006279999 | 0,006014322 |

TABLE 5.1-continued

On line determination of properties of a mixture of crude oils

| | Proximity | | Mixture 4C | | 4A | 4B |
|---|---|---|---|---|---|---|
| λ (cm-1) | Index λ (nm) | Weight | Measured | Estimated 1,04E-06 | 1,27E-06 | 1,35E-06 |
| 4460 | 2242,2 | 1 | 0,009258476 | 0,009155 72 | 0,009273227 | 0,009031317 |
| 4384 | 2281 | 1 | 0,078089814 | 0,077898 54 | 0,077667461 | 0,078139647 |
| 4332 | 2308,4 | 1 | 0,15773336 | 0,157794 6 | 0,15779336 | 0,15779336 |
| 4304 | 2323,4 | 1 | 0,104631107 | 0,104524 | 0,104179419 | 0,104867782 |
| 4260 | 2347,4 | 1 | 0,130690546 | 0,130249 58 | 0,130445533 | 0,130052183 |
| 4208 | 2376,4 | 1 | 0,087815393 | 0,087751 55 | 0,087835559 | 0,087668552 |
| 4172 | 2396,9 | 1 | 0,091208037 | 0,090879 88 | 0,090874188 | 0,090884188 |
| 4132 | 2420,1 | 1 | 0.084648925 | 0,084706 1 | 0,084659424 | 0,084767595 |
| 4104 | 2436,6 | 1 | 0,0824855 | 0,082364 77 | 0,082387661 | 0,082348493 |
| 4060 | 2463,1 | 1 | 0,087068028 | 0,087578 65 | 0,087471 71 | 0,087688219 |
| 4040 | 2475,2 | 1 | 0.067784043 | 0,068366 5 | 0,068433403 | 0,068295897 |
| Density | | | 0,8663 | 0,86555 | 0,8646 | 0,8665 |
| % Sulphur | | | 1,6 | 1,65 | 1,6 | 1,7 |
| Viscosity 100° C. | | | 2,27 | 2,265 | 2,36 | 2,17 |
| % Conradson Carbon | | | 4,8 | 5 | 4, | 5,1 |
| % Paraffin content | | | 5 | 4,95 | 4,9 | 5 |

TABLE 6.1

Determination of the Properties of a reformer feed

| Proximity Index | | Feed 6D | | 6A | 6B | 6C |
|---|---|---|---|---|---|---|
| λ (nm) | Weight | Measured | Estimated | 5,7E-A | 8,2E-5 | 9,7E-5 |
| 2210 | 1 | 0,04624 | 0,04659897 | 0,04648 | 0,04671 | 0,04659 |
| 2260 | 1 | 0,18118 | 0,18154437 | 0,18233 | 0,18132 | 0,18085 |
| 2266 | 1 | 0,25391 | 0,25482278 | 0,25605 | 0,25439 | 0,25386 |
| 2276 | 1 | 0,33866 | 0,33942652 | 0,3412 | 0,33844 | 0,33857 |
| 2286 | 1 | 0,33776 | 0,33747772 | 0,3395 | 0,33634 | 0,33652 |
| 2307 | 1 | 0,54602 | 0,54558172 | 0,54286 | 0,54922 | 0,54375 |
| 2328 | 1 | 0,38819 | 0,38770261 | 0,38812 | 0,38791 | 0,38685 |
| 2344 | 1 | 0,4557 | 0,4561672 | 0,45568 | 0,45592 | 0,45717 |
| 2376 | 1 | 0,31751 | 0,31727184 | 0,31483 | 0,32067 | 0,31543 |
| 2397 | 1 | 0,33674 | 0,33644352 | 0,33466 | 0,33858 | 0,33561 |
| 2408 | 1 | 0,31787 | 0,31746329 | 0,31737 | 0,31904 | 0,31525 |
| 2418 | 1 | 0,32524 | 0,32334235 | 0,3244 | 0,32341 | 0,32186 |
| 2437 | 1 | 0,34758 | 0,34790932 | 0,34915 | 0,34543 | 0,34996 |
| 2457 | 1 | 0,38142 | 0,38057046 | 0,3793 | 0,38076 | 0,38195 |
| % Linear Saturated | | 33,0 | 32,6 | 32,5 | 32,4 | 32,9 |
| % Isoparaffins | | 30,1 | 30,8 | 31,4 | 31,1 | 29,9 |
| % Naphthenes | | 29,3 | 29,2 | 29,2 | 28,5 | 30 |
| % Aromatics | | 7,6 | 7,4 | 6,9 | 8 | 7,2 |
| Density | | 0,7151 | 0,7158 | 0,7152 | 0,7167 | 0,7155 |

TABLE 7.1

Determination of Properties of feed to FCC reactor and yields properties of products

| | Proximity | | Feed 7D | | 7A | 7B |
|---|---|---|---|---|---|---|
| λ (cm-1) | Index λ (nm) | Weight | Measured | Estimated 1,10E-06 | 1,28E-06 | 1,30E-06 |
| 4720 | 2118,6 | 1 | 0,00024017 | 0,000283004 | 0,000238346 | 0,000327662 |
| 4672 | 2140,4 | 1 | 0,002238801 | 0,002010364 | 0,001890879 | 0,00212985 |
| 4640 | 2155,2 | 1 | 0,004237234 | 0,003903227 | 0,003874117 | 0,003932336 |
| 4612 | 2168,3 | 1 | 0,005237444 | 0,004972667 | 0,004866233 | 0,005079102 |
| 4584 | 2181,5 | 1 | 0,005332797 | 0,005055095 | 0,005031089 | 0,005079102 |
| 4484 | 2230,2 | 1 | 0,007970887 | 0,007756354 | 0,007744263 | 0,007768446 |
| 4460 | 2242,2 | 1 | 0,011303264 | 0,011210967 | 0,011212199 | 0,011209736 |
| 4384 | 2281 | 1 | 0,072994455 | 0,07273491 | 0,07292398 | 0,072545839 |
| 4332 | 2308,4 | 1 | 0,152067643 | 0,1152159348 | 0,151945649 | 0,152373047 |
| 4304 | 2323,4 | 1 | 0,100517606 | 0,100397569 | 0,100601923 | 0,100193214 |
| 4260 | 2347,4 | 1 | 0,131209247 | 0,131514201 | 0,131487607 | 0,131540794 |
| 4212 | 2374,2 | 1 | 0,091618024 | 0,09162318 92 | 0,091564633 | 0,091681751 |
| 4168 | 2399,2 | 1 | 0,094011773 | 0,094322962 | 0,09427582 | 0,094370104 |
| 4132 | 2420,1 | 1 | 0,086184908 | 0,08667531 4 | 9,086678538 | 0,086672 09 |
| 4104 | 2436,6 | 1 | 0,081457005 | 0,08191602 2 | 0,081981133 | 0,081850912 |
| 4060 | 2463,1 | 1 | 0,084267922 | 0,08431805 2 | 0,084444043 | 0,084419206 |
| 4040 | 2475,2 | 1 | 0,06911082 | 0,06914675 2 | 0,069239547 | 0,069053957 |
| Density | | | 0,926 | 0,9225 | 0,922 | 0,923 |
| % Sulphur | | | 1,97 | 1,85 | 1,83 | 1,87 |
| Aniline Point | | | 83,5 | 83,2 | 78,2 | 88,2 |
| Viscosity 100° C. | | | 8,8 | 9,1 | 8,7 | 9,5 |
| Temp. 50% distilled | | | 461 | 464 | 457 | 471 |
| KUOP | | | 11,8 | 11,85 | 11,85 | 11,9 |
| Mol. Weight | | | 450,6 | 449,95 | 434,5 | 465,4 |
| % Aromatic Carbon | | | 21,8 | 21,2 | 21,6 | 20,9 |
| CRACKABILITY | | | 2,47 | 2,57 | 2,55 | 2,59 |
| COKABILITY | | | 1,01 | 1,00 | 0,99 | 1,01 |
| GASOIL INDEX | | | 1,55 | 1,515 | 1,54 | 1,49 |
| GASOLINE INDEX | | | 0,99 | 0,985 | 0,99 | 0,98 |
| Gasoline Yield (%) | | | 45 | 44,5 | 43 | 46 |
| Residue Yield (%) | | | 12 | 11,25 | 13 | 9,5 |
| RON Clear Gasoline | | | 92,7 | 92,4 | 92,4 | 92,4 |

TABLE 8.1

On line Determination of properties of feed to hydrogenation unit for gasoline

| λ | Prox. | | Feed 8F | | 8A | 8B | 8C | 8D | 8E |
|---|---|---|---|---|---|---|---|---|---|
| (cm-1) | Index λ (nm) | Weight | Measured | Estimated 0,0000042 | 0,0000034 | 0,0000047 | 0,0000114 | 0,0000130 | 0,0000222 |
| 8949 | 1117,5 | 1 | 0,006443 | 0,0064568 | 0,006082 | 0,006957 | 0,006138 | 0,006508 | 0,006607 |
| 8795 | 1137 | 1 | 0,036107 | 0,035343 | 0,035282 | 0,035954 | 0,035428 | 0,035343 | 0,034706 |
| 8780 | 1139 | 1 | 0,039287 | 0,0385 | 0,038591 | 0,039092 | 0,038516 | 0,038491 | 0,037812 |
| 8764 | 1141 | 1 | 0,040899 | 0,040123 | 0,040341 | 0,040719 | 0,040019 | 0,040077 | 0,039461 |

TABLE 8.1-continued

On line Determination of properties of feed to hydrogenation unit for gasoline

| λ (cm-1) | Prox. Index λ (nm) | Weight | Feed 8F Measured | Feed 8F Estimated | 8A | 8B | 8C | 8D | 8E |
|---|---|---|---|---|---|---|---|---|---|
|  |  |  |  | 0,0000042 | 0,0000034 | 0,0000047 | 0,0000114 | 0,0000130 | 0,0000222 |
| 8737 | 1144,5 | 1 | 0,039495 | 0,0389040 | 0,39152 | 0,039435 | 0,038641 | 0,038923 | 0,038369 |
| 8688 | 1151 | 1 | 0,027962 | 0,027745 | 0,027983 | 0,028106 | 0,027187 | 0,027774 | 0,027677 |
| 8673 | 1153 | 1 | 0,024452 | 0,024293 | 0,024501 | 0,024562 | 0,023745 | 0,024321 | 0,024335 |
| 8651 | 1156 | 1 | 0,020612 | 0,020536 | 0,020671 | 0,020691 | 0,020084 | 0,020603 | 0,020633 |
| 8621 | 1160 | 1 | 0,018274 | 0,018286 | 0,018339 | 0,018306 | 0,018049 | 0,018386 | 0,018352 |
| 8576 | 1166 | 1 | 0,01793 | 0,018054 | 0,018108 | 0,017858 | 0,018142 | 0,018142 | 0,018028 |
| 8565 | 1167,5 | 1 | 0,018035 | 0,018177 | 0,018257 | 0,017927 | 0,018321 | 0,018248 | 0,018134 |
| 8525 | 1173 | 1 | 0,018845 | 0,01903 | 0,019164 | 0,018622 | 0,019256 | 0,019091 | 0,019015 |
| 8496 | 1177 | 1 | 0,020612 | 0,020832 | 0,020937 | 0,020371 | 0,021058 | 0,029941 | 0,020854 |
| 8446 | 1184 | 1 | 0,0274 | 0,027769 | 0,027682 | 0,027136 | 0,028172 | 0,028072 | 0,027781 |
| 8418 | 1188 | 1 | 0,031615 | 0,032149 | 0,031906 | 0,031481 | 0,032626 | 0,032571 | 0,032159 |
| 8389 | 1192 | 1 | 0,033492 | 0,034192 | 0,033845 | 0,033563 | 0,034457 | 0,034442 | 0,034203 |
| 8347 | 1198 | 1 | 0,031083 | 0,031498 | 0,031409 | 0,031279 | 0,031529 | 0,031487 | 0,031786 |
| 8326 | 1201 | 1 | 0,028905 | 0,029171 | 0,029085 | 0,029088 | 0,029138 | 0,028993 | 0,029566 |
| 8313 | 1203 | 1 | 0,027531 | 0,027733 | 0,027583 | 0,027724 | 0,027708 | 0,027492 | 0,028162 |
| 8285 | 1207 | 1 | 0,024969 | 0,0251 | 0,024832 | 0,025172 | 0,025132 | 0,024829 | 0,025537 |
| 8264 | 1210 | 1 | 0,022844 | 0,022933 | 0,022677 | 0,022977 | 0,023009 | 0,022666 | 0,023343 |
| 8203 | 1219 | 1 | 0,015306 | 0,015327 | 0,015374 | 0,015223 | 0,015542 | 0,015009 | 0,015488 |
| 8140 | 1228,5 | 1 | 0,00894 | 0,0089636 | 0,009101 | 0,008868 | 0,009078 | 0,008757 | 0,009014 |
| 8065 | 1240 | 1 | 0,004327 | 0,0043406 | 0,904467 | 0,00427 | 0,004393 | 0,004211 | 0,004363 |
| 7758 | 1289 | 1 | 0,000897 | 0,0009398 | 0,000895 | 0,00094 | 0,000918 | 0,001025 | 0,000921 |
| 8117 | 1232 | 1 | 0,005349 | 0,0053616 | 0,005304 | 0,005591 | 0,005209 | 0,005491 | 0,005213 |
| 7424 | 1347 | 1 | 0,00869 | 0,008592 | 0,008554 | 0,008798 | 0,008447 | 0,008701 | 0,008461 |
| 7396 | 1352 | 1 | 0,012209 | 0,012095 | 0,012056 | 0,012119 | 0,011922 | 0,012289 | 0,012093 |
| 7380 | 1355 | 1 | 0,015806 | 0,015784 | 0,015674 | 0,015614 | 0,015688 | 0,016136 | 0,015811 |
| 7356 | 1359,5 | 1 | 0,022613 | 0,022831 | 0,022633 | 0,022499 | 0,022915 | 0,023452 | 0,022656 |
| 7348 | 1361 | 1 | 0,024681 | 0,024929 | 0,024753 | 0,024623 | 0,025033 | 0,025538 | 0,024698 |
| 7339 | 1362,5 | 1 | 0,026435 | 0,026707 | 0,026552 | 0,026428 | 0,026818 | 0,027301 | 0,026438 |
| 7321 | 1366 | 1 | 0,029615 | 0,029773 | 0,029759 | 0,029549 | 0,029849 | 0,030217 | 0,029509 |
| 7273 | 1375 | 1 | 0,038104 | 0,038252 | 0,038215 | 0,037747 | 0,038738 | 0,038781 | 0,037777 |
| 7254 | 1378,5 | 1 | 0,042097 | 0,042361 | 0,042333 | 0,041789 | 0,042904 | 0,042934 | 0,041847 |
| 7241 | 1381 | 1 | 0,044261 | 0,044511 | 0,044521 | 0,043951 | 0,044955 | 0,045039 | 0,044087 |
| 7231 | 1383 | 1 | 0,04541 | 0,045556 | 0,045625 | 0,045014 | 0,045882 | 0,045992 | 0,045269 |
| 7199 | 1389 | 1 | 0,04833 | 0,048276 | 0,048333 | 0,047664 | 0,048684 | 0,048622 | 0,048084 |
| 7184 | 1392 | 1 | 0,049461 | 0,049347 | 0,049442 | 0,048812 | 0,049816 | 0,049597 | 0,049077 |
| 7161 | 1396,5 | 1 | 0,049514 | 0,049304 | 0,049526 | 0,049149 | 0,049522 | 0,049216 | 0,049109 |

TABLE 8.1-continued

On line Determination of properties of feed to hydrogenation unit for gasoline

| λ (cm-1) | Prox. Index λ (nm) | Weight | Feed 8F Measured | Estimated | 8A | 8B | 8C | 8D | 8E |
|---|---|---|---|---|---|---|---|---|---|
|  |  |  |  | 0,0000042 | 0,00000 34 | 0,00000 47 | 0,00001 14 | 0,00001 30 | 0,00002 22 |
| 7151 | 1398,5 | 1 | 0,04893 | 0,048706 | 0,048937 | 0,048708 | 0,048735 | 0,048454 | 0,048697 |
| 7117 | 1405 | 1 | 0,0471 | 0,04703 | 0,047083 | 0,046965 | 0,046646 | 0,046455 | 0,048003 |
| 7105 | 1407,5 | 1 | 0,046793 | 0,46839 | 0,046789 | 0,046579 | 0,046484 | 0,046242 | 0,0481 |
| 7087 | 1411 | 1 | 0,045855 | 0,046047 | 0,045894 | 0,045586 | 0,045829 | 0,045454 | 0,047474 |
| 7070 | 1414,5 | 1 | 0,043481 | 0,043682 | 0,043573 | 0,043226 | 0,043476 | 0,043002 | 0,045138 |
| 7018 | 1425 | 1 | 0,036493 | 0,036481 | 0,036252 | 0,036396 | 0,036261 | 0,035933 | 0,037564 |
| 6991 | 1430,5 | 1 | 0,037461 | 0,037372 | 0,037024 | 0,0375 | 0,037441 | 0,037171 | 0,037724 |
| 6974 | 1434 | 1 | 0,037514 | 0,037391 | 0,037162 | 0,037605 | 0,037629 | 0,037269 | 0,037298 |
| 6971 | 1434,5 | 1 | 0,037387 | 0,037261 | 0,037066 | 0,037486 | 0,037496 | 0,037135 | 0,037127 |
| 6930 | 1443 | 1 | 0,032307 | 0,032112 | 0,032218 | 0,032451 | 0,032217 | 0,031884 | 0,03179 |
| 6849 | 1460 | 1 | 0,022126 | 0,021897 | 0,022177 | 0,022295 | 0,021806 | 0,021642 | 0,021565 |
| 6824 | 1465,5 | 1 | 0,021591 | 0,021377 | 0,021682 | 0,021745 | 0,021384 | 0,021155 | 0,02092 |
| 6752 | 1481 | 1 | 0,018013 | 0,01796 | 0,018203 | 0,018411 | 0,017735 | 0,017774 | 0,017678 |
| 6720 | 1488 | 1 | 0,016098 | 0,016058 | 0,016257 | 0,016607 | 0,015759 | 0,015855 | 0,015811 |
| 6693 | 1494 | 1 | 0,014581 | 0,014542 | 0,014741 | 0,015042 | 0,01436 | 0,01435 | 0,014155 |
| 6614 | 1512 | 1 | 0,010568 | 0,01045 | 0,010546 | 0,011075 | 0,010321 | 0,010193 | 0,010114 |
| 6566 | 1523 | 1 | 0,007881 | 0,007794 | 0,007827 | 0,008432 | 0,007533 | 0,007562 | 0,007616 |
| 6536 | 1530 | 1 | 0,007116 | 0,007114 | 0,00711 | 0,007727 | 0,006783 | 0,006993 | 0,0069S7 |
| 6481 | 1543 | 1 | 0,005233 | 0,0052664 | 0,005299 | 0,005895 | 0,004821 | 0,005154 | 0,005163 |

|  | GA 612 | Estimé | GA 616 | GA 621 | GA 406 | GA 420 | GM 452 |
|---|---|---|---|---|---|---|---|
| % Linear Saturated | 8,73 | 8,96 | 7,73 | 7,98 | 10,65 | 18,86 | 9,59 |
| % Isoparaffins | 6,83 | 7,35 | 6,51 | 6,62 | 8,8 | 8,26 | 6,56 |
| % Naphthenes | 5,83 | 5,73 | 6,38 | 6,93 | 5,56 | 4,87 | 4,95 |
| % Linear Olefins | 11,33 | 11,92 | 12,41 | 12,09 | 10,49 | 11,33 | 13,28 |
| % Cyclic Olefins | 12,79 | 12,77 | 12,99 | 13,68 | 12,94 | 11,81 | 12,44 |
| % Benzene | 22,46 | 21,74 | 21,35 | 21,38 | 23,34 | 21,53 | 21,1 |
| % Toluene | 13,72 | 13,63 | 13,71 | 13,51 | 13,55 | 13,18 | 14,18 |
| % Xylene | 5,08 | 6,74 | 5,97 | 5,57 | 4,89 | 11,36 | 5,9 |
| % Alkyl benzene | 5,96 | 5,94 | 5,98 | 5,6 | 5,11 | 6,84 | 6,16 |
| % Dienes | 16,44 | 15,90 | 17,67 | 17,94 | 14,83 | 13,57 | 15,47 |
| DENSITY | 0,8124 | 0,8066 | 0,8133 | 0,8097 | 0,8012 | 0,803 | 0,8058 |
| Yield light cut | 25,7 | 26,7 | 24,6 | 25,1 | 28,5 | 27,5 | 27,8 |
| Yield heavy cut | 40,3 | 39,4 | 41,7 | 41,2 | 35,7 | 39,7 | 38,7 |
| Tield raffinate | 13,7 | 13.3 | 13,5 | 13,4 | 13,7 | 12,4 | 13,5 |
| Yield benzene | 20,3 | 20,6 | 20,2 | 20,3 | 22,1 | 20,4 | 20,0 |

TABLE 9.1

Determination of MON of a reformate

| Proximity Index λ (cm − 1) (nm)² | Weight | Reformate 9A Measured | Estimated 0,0000581 24 | 9B 0,00006 398 | 9C 0,00006 638 | 9D 0,00018 149 | 9E 0,00018 529 | 9F 0,00019 385 |
|---|---|---|---|---|---|---|---|---|
| 4720 | 2119 | 1 | 0,001098 | ?? | 0,00120 43 | 0,00123 59 | 0,00076 051 | 0,00108 01 | 0,00091 553 |
| 4670 | 2141 | 1 | 0,017744 | ?? | 0,018971 | 0,016537 | 0,014737 | 0,015558 | 0,015581 |

TABLE 9.1-continued

Determination of MON of a reformate

Reformate 9A

| Proximity Index λ (cm − 1) | (nm)² | Weight | Measured | Estimated 0,00005 8124 | 9B 0,00006 398 | 9C 0,00006 638 | 9D 0,00018 149 | 9E 0,00018 529 | 9F 0,00019 385 |
|---|---|---|---|---|---|---|---|---|---|
| 4640 | 2155 | 1 | 0,038144 | ?? | 0,019076 | 0,016358 | 0,014281 | 0,0159 | 0,015344 |
| 4615 | 2167 | 1 | 0,024297 | ?? | 0,025324 | 0,021903 | 0,019435 | 0,023414 | 0,021006 |
| 4585 | 2181 | 1 | 0,020515 | ?? | 0,020612 | 0,017869 | 0,016021 | 0,016114 | 0,016429 |
| 4485 | 2230 | 1 | 0,012619 | ?? | 0,011885 | 0,011415 | 0,010242 | 0,011366 | 0,010529 |
| 4460 | 2242 | 1 | 0,018197 | ?? | 0,017006 | 0,016221 | 0,015362 | 0,016719 | 0,015344 |
| 4385 | 2281 | 1 | 0,092064 | ?? | 0,089813 | 0,090082 | 0,09165 | 0,094457 | 0,088586 |
| 4332 | 2308 | 1 | 0,12886 | ?? | 0,12812 | 0,13172 | 0,12815 | 0,1269 | 0,13463 |
| 4305 | 2323 | 1 | 0,11882 | ?? | 1,11606 | 0,11689 | 0,1205 | 0,12271 | 0,11448 |
| 4260 | 2347 | 1 | 0,098322 | ?? | 0,09716 | 0,10023 | 0,099018 | 0,9446 | 0,10223 |
| 4210 | 2375 | 1 | 0,064577 | ?? | 0,063284 | 0,065124 | 0,066654 | 0,065915 | 0,06736 |
| 4170 | 2398 | 1 | 0,061405 | ?? | 0,060439 | 0,063425 | 0,067026 | 0,065132 | 0,065986 |
| 4135 | 2418 | 1 | 0,059296 | ?? | 0,058485 | 0,051794 | 0,065184 | 0,063244 | 0,062684 |
| 4105 | 2436 | 1 | 0,06198 | ?? | 0,061975 | 0,064438 | 0,066333 | 0,002071 | 0,066088 |
| 4060 | 2463 | 1 | 0,11037 | ?? | 0,11022 | 0,1131 | 0,11289 | 0,10222 | 0,1122 |
| 4040 | 2475 | 1 | 0,091698 | ?? | 0,094281 | 0,091661 | 0,091751 | 0,096914 | 0,090604 |
| MON |  | 0 | ∞ | ?? | 88,3 | 86,2 | 87,2 | 89,2 | 82,4 |

TABLE 9.2

"Sample" MC1 obtained by densification

| Fraction in Mixture λ (cm − 1) | λ (nm) | MC1 | 9B 0,889 | 9D −0,276 | 9G 0,387 |
|---|---|---|---|---|---|
| 4720 | 2119 | 0,001175932 | 0,0012043 | 0,00076051 | 0,00081253 |
| 4670 | 2141 | 0,017365599 | 0,018971 | 0,014737 | 0,011765 |
| 4640 | 2155 | 0,017767782 | 0,019076 | 0,014281 | 0,012239 |
| 4615 | 2167 | 0,024118931 | 0,025324 | 0,019435 | 0,01796 |
| 4585 | 2181 | 0,019041012 | 0,020612 | 0,016021 | 0,013237 |
| 4485 | 2230 | 0,011987639 | 0,011885 | 0,010242 | 0,010952 |
| 4460 | 2242 | 0,017122848 | 0,017086 | 0,015362 | 0,015912 |
| 4385 | 2281 | 0,091829933 | 0,089813 | 0,09165 | 0,096098 |
| 4332 | 2308 | 0,1300549 | 0,12812 | 0,12815 | 0,13281 |
| 4305 | 2323 | 0,11911918 | 0,11606 | 0,1205 | 0,12682 |
| 4260 | 2347 | 0,09859607 | 0,09716 | 0,099018 | 0,10194 |
| 4210 | 2375 | 0,064520009 | 0,063284 | 0,066654 | 0,068709 |
| 4170 | 2398 | 0,061986802 | 0,060439 | 0,067026 | 0,068963 |
| 4135 | 2418 | 0,060186195 | 0,058485 | 0,065184 | 0,06749 |
| 4105 | 2436 | 0,062468569 | 0,061975 | 0,066333 | 0,066187 |
| 4060 | 2463 | 0,110237982 | 0,11622 | 0,11289 | 0,098096 |
| 4040 | 2475 | 0,093415832 | 0,094281 | 0,091751 | 0,090004 |
| MON00 |  | 88,4 | 88,3 | 87,2 | 87,6 |

TABLE 9.3

"Sample" MC1 obtained by densification

| Fraction in Mixture λ (cm − 1) | λ (nm) | MC2 | 9B 1,162 | 9C 0,24 | 9D −0,402 |
|---|---|---|---|---|---|
| 4720 | 2119 | 0,001178718 | 0,0012043 | 0,00035436 | 0,00076051 |
| 4670 | 2141 | 0,017275892 | 0,018971 | 0,0048161 | 0,014737 |
| 4640 | 2155 | 0,01792139 | 0,019076 | 0,0062335 | 0,014281 |
| 4615 | 2167 | 0,02374750 | 0,025324 | 0,0088912 | 0,019435 |
| 4585 | 2181 | 0,019544078 | 0,020612 | 0,0084724 | 0,016021 |
| 4485 | 2230 | 0,011946806 | 0,011885 | 0,0093905 | 0,010242 |
| 4460 | 2242 | 0,017153608 | 0,017086 | 0,01448 | 0,015362 |
| 4385 | 2281 | 0,091428926 | 0,089813 | 0,099623 | 0,09165 |
| 4332 | 2308 | 0,13153274 | 0,12812 | 0,14239 | 0,12815 |
| 4305 | 2323 | 0,11829752 | 0,11606 | 0,13282 | 0,1205 |
| 4260 | 2347 | 0,09879868 | 0,09716 | 0,1071 | 0,099018 |
| 4210 | 2375 | 0,06434942 | 0,063284 | 0,073368 | 0,066654 |
| 4170 | 2398 | 0,061427506 | 0,060439 | 0,075591 | 0,067026 |
| 4135 | 2418 | 0,059908962 | 0,058485 | 0,075639 | 0,065184 |
| 4105 | 2436 | 0,062810524 | 0,061975 | 0,072756 | 0,066333 |
| 4060 | 2463 | 0,11139522 | 0,11622 | 0,090539 | 0,11289 |
| 4040 | 2475 | 0,09128022 | 0,094281 | 0,07754 | 0,091751 |

TABLE 9.3-continued

"Sample" MC1 obtained by densification

| Fraction in Mixture λ (cm − 1) | λ (nm) | MC2 | 9B | 9C | 9D |
|---|---|---|---|---|---|
| | | | 1,162 | 0,24 | −0,402 |
| MON00 | | 88,2 | 88,3 | 86 | 87,2 |

TABLE 9.4

Determination of MON of reformate based on "Samples" generated

Reformate 9A

| Proximity Index λ (cm − 1) | λ (nm) | Weight | Measured | Estimated 0,0000092 71 | MC1 0,00001 0043 | MC2 0,00001 3457 |
|---|---|---|---|---|---|---|
| 4720 | 2119 | 1 | 0,0010981 | 0,0011773 | 0,0011759 | 0,0011787 |
| 4670 | 2141 | 1 | 0,017744 | 0,017321 | 0,017366 | 0,017276 |
| 4640 | 2155 | 1 | 0,018144 | 0,017845 | 0,017768 | 0,017922 |
| 4615 | 2167 | 1 | 0,024297 | 0,0239335 | 0,024119 | 0,023748 |
| 4585 | 2181 | 1 | 0,020515 | 0,0192925 | 0,019041 | 0,019544 |
| 4485 | 2230 | 1 | 0,012619 | 0,011968 | 0,011988 | 0,011948 |
| 4460 | 2242 | 1 | 0,018197 | 0,0171385 | 0,017123 | 0,017154 |
| 4385 | 2281 | 1 | 0,092064 | 0,0916295 | 0,09183 | 0,091429 |
| 4332 | 2308 | 1 | 0,12886 | 0,130795 | 0,13006 | 0,13153 |
| 4305 | 2323 | 1 | 0,11882 | 0,11871 | 0,11912 | 0,1183 |
| 4260 | 2347 | 1 | 0,098322 | 0,098697 | 0,098596 | 0,098798 |
| 4210 | 2375 | 1 | 0,064577 | 0,064435 | 0,064452 | 0,064435 |
| 4170 | 2398 | 1 | 0,061405 | 0,0617075 | 0,0619787 | 0,0614287 |
| 4135 | 2418 | 1 | 0,059296 | 0,0600475 | 0,060186 | 0,0599099 |
| 4105 | 2436 | 1 | 0,06198 | 0,06264 | 0,0624699 | 0,0628101 |
| 4060 | 2463 | 1 | 0,11037 | 0,110815 | 0,11024 | 0,11139 |
| 4040 | 2475 | 1 | 0,091698 | 0,092348 | 0,093416 | 0,09128 |
| MON00 | | 0 | 88 | 88,3 | 88,4 | 88,2 |

TABLE 9.5

| Proximity Index λ (cm − 1) | λ (nm) | Weight | Measured | Estimated 0,00001223 5 | 9A 0,00001223 5 |
|---|---|---|---|---|---|
| 4720 | 2119 | 1 | 0,0010702 | 0,0010981 | 0,0010981 |
| 4670 | 2141 | 1 | 0,0171 | 0,017744 | 0,017744 |
| 4640 | 2155 | 1 | 0,017768 | 0,018144 | 0,018144 |
| 4615 | 2167 | 1 | 0,024103 | 0,024297 | 0,024297 |
| 4585 | 2181 | 1 | 0,020269 | 0,020515 | 0,020515 |
| 4485 | 2230 | 1 | 0,012224 | 0,012619 | 0,012619 |
| 4460 | 2242 | 1 | 0,018338 | 0,018197 | 0,018197 |
| 4385 | 2281 | 1 | 0,091998 | 0,092064 | 0,092061 |
| 4332 | 2308 | 1 | 0,1306 | 0,12886 | 0,12886 |
| 4365 | 2323 | 1 | 0,11841 | 0,11882 | 0,11882 |
| 4260 | 2347 | 1 | 0,098802 | 0,098322 | 0,098322 |
| 4210 | 2375 | 1 | 0,06262 | 0,064577 | 0,064577 |
| 4170 | 2398 | 1 | 0,060234 | 0,061405 | 0,061405 |
| 4135 | 2418 | 1 | 0,059762 | 0,059296 | 0,059296 |
| 4105 | 2436 | 1 | 0,062527 | 0,06198 | 0,06198 |
| 4060 | 2463 | 1 | 0,11151 | 0,11037 | 0,11037 |
| 4040 | 2475 | 1 | 0,092677 | 0,091698 | 0,091698 |
| MON00 | | | 87,9 | 88 | 88 |

We claim:

1. A method of determining or predicting a value $P_x$ which is a value of a property of a material X or a property of a product of a process from said material or yield of said process, which method comprises measuring the absorption $D_{ix}$ of said material at more than one wavelength in the region 600–2600 nm, comparing the said absorptions or a derivative thereof with absorptions $D_{im}$ or derivatives thereof at the same wavelength for a number of standards S in a bank for which the said property or yield P is known, and choosing from the bank at least one standard $S_m$ with property $P_m$ said standard having the smallest average value of the absolute difference at each wavelength I between the absorption $D_ix$ (or derivative thereof) for the material and the absorption $D_im$ (or derivative thereof) for the standard $S_m$ to obtain $P_x$, with averaging of said properties or yields $P_m$ when more than one standard $S_m$ is chosen and wherein the standard $S_m$ chosen for the property or yield wanted is such that in relation to the unknown material X and each chosen standard $S_m$ a function $i_{xm}$, which is a proximity index defined by $i^2(xm)=\Sigma(D_{ix}D_{im})^2$, is less than a minimal index $i_m$ which has been determined from preselected standards by (a) calculating for each pair of the standards a value of a corresponding proximity index to obtain a series of proximity indices with corresponding property differences, (b) relating values of the proximity indices to corresponding property differences, (c) calculating an average of the corresponding property differences for predetermined values L which are greater than a corresponding proximity index, and (d) calculating the minimal index based on the average property differences and a reproducibility standard for the property.

2. A method according to claim 1, wherein the properties of synthetic standards, which are mixtures, and their spectra for consideration for possible choice for $S_m$ are estimated from existing standards in the bank for which, in respect of each existing standard for use in said mixture equation (4) and (5) are met, $$(Min)Cj-uj \leq Cj \leq (Max)Cj+uj \qquad (4)$$

and $$\Sigma Cj=1 \qquad (5)$$

wherein $C_j$ is fraction of component j in the sample i, Min $C_j$ is the minimum of j in the samples for which the method is to be used, Max $C_j$ is the maximum of j in the samples for which the method is to be used, and uj is between 1.0 and 0.05.

3. A method according to claim 2 wherein at least one of (i) the estimated Standards and the corresponding spectra, and (ii) the property $P_x$ of the unknown material and its spectrum, are added to the bank.

4. A method according to claim 1 wherein properties of standards and spectra for consideration for possible choice are estimated by interpolation from measured properties of standards and spectra for which the proximity index with respect to the unknown X is not more than 10 times the minimal Index.

5. A method according to claim 1 wherein the property is a physicochemical property of material X.

6. A method according to claim 1 wherein the property is a physicochemical property or yield of a product of a process to which at least one material X is a feed.

7. A method according to claim 1 wherein said process is a hydrocarbon conversion or separation process.

8. A method according to claim 7 wherein said process is a distillation to give at least 1 distillation product and a residue and the properties/yields are obtained in respect of said product and/or residue.

9. A method according to claim 7 wherein said process is a reforming or catalytic cracking or hydrotreatment, or distillation or blending.

10. A method according to claim 1 wherein said property is in respect of a motor fuel and is at least one of an Octane Number, vapour pressure, volatility percentage distilled at 70° and at 100° C., gum content in mg/100 ml and content of sulphur, benzene or methyl tert. butyl ether.

11. A method according to claim 10 wherein the property is in respect of a blend comprising gasoline, the spectra are measured on feeds to said blending, and by calculation the blend index obtained as a linear or non linear function.

12. A method according to claim 1 wherein said property is in respect of gas oil and is at least one of cetane index, cetane number, percentage of sulphur, density at 15° C., clear point, cloud point, filtrability and viscosity at 40° C.

13. A method according to claim 1 wherein said property is in respect of a crude oil and is at least one of density, percentage of sulphur, viscosity at 100° C., content of paraffin and residual carbon percentage (Conradson Carbon).

14. A method according to claim 1 wherein said property is in respect of a feed to a reforming process and is at least one of percentages of saturated linear, isoparaffins, napthenes, and aromatics and density.

15. A method according to claim 1 wherein said property is in respect of a feed to a fluid catalytic cracking unit and is at least one of the density, the weight percentage of sulphur, the aniline point, viscosity at 100° C., refractive index at 20° C. or 60° C., 50% distillation point, molecular weight, percentage of aromatic carbon and the KUOP, crackability or cokability of the feed or yield of gas, gasoline, gas oil or residue.

16. A method according to claim 1 wherein said percentage is in respect of the feed to a hydrogenation unit and is at least one of percentages of linear saturation, isoparaffins, naphthenes, linear olefins, cylic olefins, benzene, toluene xylene, alkylbenzene, density, or yield of light cut, heavy cut, or raffinate or benzene.

17. A method according to claim 1 wherein the said property or yield of said process is used to control and optimise said process.

18. A method according to claim 1 wherein selected steps are computer implemented.

19. A method according to claim 18 wherein the selected steps include assessing, comparing and choosing.

20. Apparatus suitable for use in the method of claim 1 which comprises an NIR spectrometer receiving at least one signal from a feed or product line in said process and being coupled to a computer to effect continuous measurement of the spectra of the feed and/or product and provide feed back control of the process.

21. A method according to claim 1 wherein the property is a physicochemcial property of material X and wherein said property is in respect of a motor fuel and is at least one of an Octane Number, vapour pressure, volatility percentage distilled at 70° and at 100° C., gum content in mg/100 ml and content of sulphur, benzene or methyl tert. butyl ether.

22. A method according to claim 21 wherein said property or yield of said process is used to control and optimise said process.

23. A method according to claim 1 wherein the property is a physicochemcial property of material X and wherein said property is in respect of gas oil and is at least one of cetane index, cetane number, percentage of sulphur, density at 15° C., clear point, cloud point, filterability and viscosity at 40° C.

24. A method according to claim 23 wherein said property or yield of said process is used to control and optimise said process.

25. A method according to claim 1 wherein the property is a physicochemcial property or yield of a product of a process to which at least one material X is a feed and wherein said property is in respect of a motor fuel and is at least one of an Octane Number, vapour pressure, volatility percentage distilled at 70° and at 100° C., gum content in mg/100 ml and content of sulphur, benzene or methyl tert. butyl ether.

26. A method according to claim 25 wherein said property or yield of said process is used to control and optimise said process.

27. A method according to claim 1 wherein the property is a physicochemcial property or yield of a product of a process to which at least one material X is a feed and wherein said property is in respect of gas oil and is at least one of cetane index, cetane number, percentage of sulphur, density at 15° C., clear point, cloud point, filterability and viscosity at 40° C.

28. A method according to claim 27 wherein said property or yield of said process is used to control and optimise said process.

29. A method for adding an extra synthetic standard to a bank of known standards, each of which relates at least one absorption in the 600–2600 mm region (or derivative thereof) of a known material to a known property related to that material, which property is of said material, or is of a product of a process from said material or yield of said process, which method comprises choosing from the bank at least 2 standards for which equations 4 and 5 are met, $$(Min)C_j - u_j \leq C_j \leq (Max)C_j + u_j \quad (4)$$

and $$\Sigma C_j = 1 \quad (5)$$

wherein $C_j$ is fraction of component j in a sample i, Min $C_j$ is the minimum of j in samples for which the method is to be used, Max $C_j$ is the maximum of j in the samples for which the method is to be used, and uj is between 1.0 and 0.05, considering mixing the chosen standards in at least one proportion to produce at least one mixture for use in a synthetic standard, and estimating the spectrum of said mixture according to equation 6

$$S_{mi} = \Sigma C_{ij} \times S_j$$

where Sj is the spectrum in the mixture of component j in the calibration matrix, and estimating a property of said mixture according to equation 7

$$P_{mi} = \Sigma C_{ij} \times P_j$$

where $P_j$ is the property of component j, and then adding the spectrum and property of each "mixture" to the bank, and using them in at least one model involving a correlation/regression approach to relate NIR spectra to at least one property.

30. A computer programmed to perform the method of determining or predicting a value $P_x$ which is a value of a property of a material X or a property of a product of a process from said material or yield of said process, which method comprises measuring the absorption $D_{ix}$ of said material at more than one wavelength in the region 600–2600 nm comparing the said absorptions or a derivative thereof with absorptions $D_{im}$ or derivatives thereof at the same wavelength for a number of standards S in a bank for which the said property or yield P is known, and choosing from the bank at least one standard $S_m$ with property $P_m$ said standard having the smallest average value of the absolute difference at each wavelength I between the absorption $D_i x$ (or derivative thereof) for the material and the absorption $D_i m$ (or derivative thereof) for the standard $S_m$ to obtain $P_x$, with averaging of said properties or yields $P_m$ when more than one standard $S_m$ is chosen and wherein the standard $S_m$ chosen for the property or yield wanted is such that in relation to the unknown material X and each chosen standard $S_m$ a function $i_{xm}$, which is a proximity index defined by $i^2(xm) = \Sigma(D_{ix}D_{im})^2$, is less than a minimal index $i_m$ which has been determined from preselected standards by (a) calculating for each pair of the standards a value of a corresponding proximity index to obtain a series of proximity indices with corresponding property differences, (b) relating values of the proximity indices to corresponding property differences, (c) calculating an average of the corresponding property differences for predetermined values L which are greater than a corresponding proximity index, and (d) calculating the minimal index based on the average property differences and a reproducibility standard for the property.

31. A computer programmed to perform the method of adding an extra synthetic standard to a bank of known standards, each of which relates at least one absorption in the 600–2600 nm region (or derivative thereof) of a known material to a known property related to that material, which property is of said material or is of a product of a process from said material or yield of said process, which method comprises choosing from the bank at least 2 standards for which equations 4 and 5 are met, $$(Min)Cj - uj \leq Cj \leq (Max)Cj + uj \quad (4)$$

and $$\Sigma Cj = 1 \quad (5)$$

wherein $C_j$ is fraction of component j in a sample i, Min $C_j$ is the minimum of j in samples for which the method is to be used, Max $C_j$ is the maximum of j in the samples for which the method is to be used, and uj is between 1.0 and 0.05, considering mixing the chosen standards in at least one proportion to produce at least one mixture for use in a synthetic standard, and estimating the spectrum of said mixture according to equation 6

$$S_{mi} = \Sigma C_{ij} X S_j$$

where $S_j$ is the spectrum in the mixture of component j in the calibration matrix, and estimating a property of said mixture according to equation 7

$$P_{mi} = \Sigma C_{ij} X P_j$$

where $P_j$ is the property of component j, and then adding the spectrum and property of each "mixture" to the bank, and using them in at least one model involving a correlation/regression approach to relate NIR spectra to at least one property.

32. A computer implemented method for a system including a spectrometer linked to a process line containing a material X, which is a product of a process or feed to a process, a computer linked to the spectrometer, and a controller linked to the computer and the process line, the computer including databanks having stored therein absorptions of standard materials and corresponding properties of said materials, or of products of a process from said materials or yield of said process, the method comprises steps of:

measuring absorption at more than one wavelength in the region 600–2600 nm at the process line and producing absorption signals by the spectrometer in accordance therewith;

assessing the databanks of the computer in accordance with the absorption signals;

comparing, by the computer, the absorption signals to the absorptions of the standard materials stored in the databanks;

choosing at least one standard based on the comparing, said standard having the smallest average value of the absolute difference at each wavelength i between the absorption (or derivative thereof) for the material and the absorption (or derivative thereof) for the standards, with averaging of said properties or yields when more than one standard is chosen, and controlling said process line in accordance with the outputted property/yield, wherein the standard chosen for the property or yield wanted is such that in relation to the unknown material X and each chosen standard a function $i_{xm}$, which is a proximity index defined by $i^2(xm) = \Sigma(D_{ix}D_{im})^2$, is less than a minimal index $i_m$ which has been determined from preselected standards by (a) calculating for each pair of the standards a value of a corresponding proximity index to obtain a series of proximity indices with corresponding property differences, (b) relating values of the proximity indices to corresponding property differences, (c) calculating an average of the corresponding property differences for predetermined values L which are greater than a corresponding proximity index, and (d) calculating the minimal index based on the average property differences and a reproducibility standard for the property.

* * * * *

UNITED STATES PATENT AND TRADEMARK OFFICE
CERTIFICATE OF CORRECTION

PATENT NO. : 5,712,797
DATED : January 27, 1998
INVENTOR(S) : Bernard Descales et al.

It is certified that error appears in the above-indentified patent and that said Letters Patent is hereby corrected as shown below:

Title Page, Box 30, delete "(GB) United Kingdom"

and insert therefor: ---(EP) European Patent Office---.

Signed and Sealed this

Twelfth Day of January, 1999

Attest:

Attesting Officer

Acting Commissioner of Patents and Trademarks